(12) United States Patent
Ahrens et al.

(10) Patent No.: US 9,649,393 B2
(45) Date of Patent: May 16, 2017

(54) MAGNETIC RESONANCE IMAGING CELL LABELING METHODS AND COMPOSITIONS

(71) Applicants: Carnegie Mellon University, Pittsburgh, PA (US); University of Pittsburgh - of the Commonwealth Systems of Higher Education, Pittsburgh, PA (US)

(72) Inventors: Eric T. Ahrens, Pittsburgh, PA (US); David Schwartzman, Pittsburgh, PA (US)

(73) Assignees: University of Pittsburgh-of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 637 days.

(21) Appl. No.: 14/028,870

(22) Filed: Sep. 17, 2013

(65) Prior Publication Data

US 2014/0093452 A1    Apr. 3, 2014

Related U.S. Application Data

(60) Provisional application No. 61/701,995, filed on Sep. 17, 2012, provisional application No. 61/788,887, filed on Mar. 15, 2013.

(51) Int. Cl.
*A61K 49/10* (2006.01)
*A61K 49/00* (2006.01)
*A61K 49/04* (2006.01)

(52) U.S. Cl.
CPC .......... *A61K 49/10* (2013.01); *A61K 49/0471* (2013.01)

(58) Field of Classification Search
CPC .......... A61B 5/00; A61K 49/00; A61K 49/10
See application file for complete search history.

(56) References Cited

U.S. PATENT DOCUMENTS

| | | | | |
|---|---|---|---|---|
| 4,378,347 A | * | 3/1983 | Franco | A61K 38/1825 424/565 |
| 5,196,348 A | * | 3/1993 | Schweighardt | A61K 49/06 436/173 |
| 6,460,800 B1 | * | 10/2002 | Watanabe | B43M 99/00 206/11 |
| 2007/0024641 A1 | * | 2/2007 | Nakamura | H04N 5/3454 345/620 |

OTHER PUBLICATIONS

Ahrens et al., "In vivo imaging platform for tracking immunotherapeutic cells" Nature Biotechnology, vol. 23 No. 8, Nature Publishing Group, pp. 983-987, Aug. 2005.
Ahrens et al., "Rapid quantification of inflammation in tissue samples using perfluorocarbon emulsion and fluorine-19 nuclear magnetic resonance", BioTechniques, vol. 50, No.
Kadayakkara et al., "Assaying macrophage activity in a murine model of inflammatory bowel disease using fluorine-19 MRI", Laboratory Investigation, vol. 92, pp. 636-645, A.

* cited by examiner

*Primary Examiner* — Jake Vu
*Assistant Examiner* — Jagadishwar Samala

(57) ABSTRACT

The disclosure provides, in part, fluorocarbon imaging reagents and methods for image-guided treatment and/or diagnosis of a subject with a condition associated with an inflammatory response in an internal organ. The disclosure additionally provides methods for image-guided treatment of myocardial infarction (MI) in a subject.

36 Claims, 10 Drawing Sheets

MAGNETIC RESONANCE IMAGING CELL LABELING METHODS AND COMPOSITIONS

RELATED APPLICATIONS

This application claims priority to and the benefit of the filing date of U.S. Provisional Patent Applications Nos. 61/701,995, filed Sep. 17, 2012, and 61/788,887, filed Mar. 15, 2013.

BACKGROUND

Cells of the immune system are recruited from the bloodstream to areas of tissue inflammation, damage or infection, resulting in an accumulation of immune cells at the affected site. A marked infiltration of immune cells often occurs in injured or diseased organs. For example, myocardial infarction (MI) is such an injury. In this process, myocardial tissue comprising a portion of the left ventricle (LV) is injured because it is denied oxygen acutely. This insult sets off a sequence of inflammatory events that culminates in replacement of functional myocardial tissue with non-functional scar tissue. The diminished pumping efficiency in the scarred LV places stress on the remaining viable LV myocardium, which becomes dysfunctional over time, eventually forming more scar tissue. This "scar begetting" phenomenon underlies the clinical sequelae of MI, including heart failure and arrhythmias, which engender mortality, morbidity, and high cost.

With the goal of minimizing scar burden, the optimum time to intervene after MI is early, before the default pathways have had time to replace dead LV myocardium with scar. Over the past several years, there has been increasing interest in manipulating these pathways so as to convince the body to replace dead myocardium with new, functional myocardium. This interest centers on the introduction of biological materials, including certain cells (e.g., stem and/or precursor cells) and/or proteins that possess such manipulative capabilities.

MI is just one example in which internal organs are injured; resulting in inflammation and possible scarring. More generally, there remains a need for accurate delivery of medicaments to injured internal organs, as well as precise diagnosis of abnormalities and lesions associated with internal organs.

SUMMARY

In certain aspects, the disclosure provides a method for image-guided treatment of a subject with a condition associated with an inflammatory response in an internal organ comprising administering a fluorine-19 ($^{19}F$) magnetic resonance imaging (MRI) fluorocarbon imaging reagent to said subject to label inflammatory cells, performing $^{19}F$ MRI of the subject to detect labeled inflammatory cells, identifying, for the internal organ, boundaries between healthy and affected tissue in the subject using the $^{19}F$ MRI data, and administering a medicament to the internal organ based on the boundary data to treat the condition.

In certain embodiments, the method comprises performing $^{19}F$ MRI in a region of interest of the subject. In certain embodiments, the method further comprises performing proton ($^1H$) MRI and using the $^1H$ MRI data in the analysis. In certain embodiments, the method uses the data as a 3D pattern of the inflammation and/or of the affected tissue for guiding delivery of the medicament.

In certain embodiments, the method comprises administering the medicament at one or more boundaries between healthy and affected tissue. In certain embodiments, the internal organ is selected from the group consisting of heart, kidney, bladder, liver, pancreas, intestine (colon or small intestine), appendix, esophagus, stomach, rectum, prostate, uterus, ovary, gall bladder, lung, brain, spinal cord, or spleen. In certain embodiments, the internal organ is the heart. In certain embodiments, the condition associated with an inflammatory response is cardiac arrest or myocardial infarction. In certain embodiments, the condition associated with an inflammatory response is cancer. In certain embodiments, the internal organ is inflamed (e.g., has one or more regions of inflammation).

In certain aspects, the disclosure provides a method for image-guided treatment of myocardial infarction (MI) in a subject comprising administering a $^{19}F$ MRI fluorocarbon imaging reagent to said subject to label inflammatory cells, performing $^{19}F$ MRI of the subject to detect labeled inflammatory cells, identifying boundaries between healthy and affected cardiac tissue in the subject using the $^{19}F$ MRI data, and administering a medicament to the heart based on the boundary data to treat the condition.

In certain embodiments, the method is performed within one day of the MI. In certain embodiments, the method is performed within three days of the MI. In certain embodiments, the method is performed within 3-7 days of the MI. In certain embodiment, the method comprises performing $^{19}F$ MRI in a region of interest of the subject.

In certain embodiments, the method comprises administering the medicament at one or more boundaries between healthy and affected tissue. In certain embodiments, the method further comprises performing $^1H$ MRI and using the $^1H$ MRI data in the analysis. In certain embodiments, the method uses the data as a 3D pattern of the inflammation and/or of the affected tissue for guiding delivery of the medicament.

In certain aspects, the disclosure provides a method for image-guided treatment of a subject with a condition associated with an inflammatory response in an internal organ comprising providing $^{19}F$ MRI data identifying boundaries between healthy and affected tissue of the internal organ of the subject, which subject was previously administered a $^{19}F$ MRI fluorocarbon imaging reagent to label inflammatory cells, and administering a medicament to the internal organ based on the data to treat the condition.

In certain embodiments, the method comprises administering the medicament at one or more boundaries between healthy and affected tissue. In certain embodiments, the internal organ is selected from the group consisting of heart, kidney, bladder, liver, pancreas, prostate, uterus, ovary, intestine (colon or small intestine), appendix, esophagus, stomach, rectum, gall bladder, lung, brain, spinal cord, or spleen. In certain embodiments, the internal organ is the heart. In certain embodiments, the condition associated with an inflammatory response is cardiac arrest or myocardial infarction. In certain embodiments, the condition associated with an inflammatory response is cancer. In certain embodiments, the internal organ is inflamed.

In certain aspects, the disclosure provides a method for image-guided diagnosis of a subject with a condition associated with an inflammatory response in an internal organ comprising administering a $^{19}F$ MRI fluorocarbon imaging reagent to said subject to label inflammatory cells, performing $^{19}F$ MRI of the subject to detect labeled inflammatory cells, identifying, for the internal organ, boundaries between healthy and affected tissue in the subject using the $^{19}F$ MRI data, and performing a diagnostic procedure on the internal organ based on the boundary data.

In certain embodiments, the internal organ is selected from the group consisting of heart, kidney, bladder, liver, pancreas, intestine, prostate, uterus, ovary, appendix, esophagus, stomach, rectum, gall bladder, lung, brain, spinal cord, or spleen. In certain embodiments, the internal organ is the heart. In certain embodiments, the condition is cardiac arrest or myocardial infarction. In certain embodiments, the organ is a transplanted organ. In certain embodiments, the internal organ is inflamed. In certain embodiments, the diagnostic procedure is a tissue biopsy.

In certain aspects, the disclosure provides the use of a $^{19}$F MRI fluorocarbon imaging reagent for image-guiding the treatment of a subject with a condition associated with an inflammatory response in an internal organ. In certain embodiments, the image guided treatment or biopsy may be performed in situ in the MRI instrument using suitable non-magnetic, MRI-compatible surgical instruments for delivery of therapeutics or biopsy collection. In other embodiments, the image-guided treatment or biopsy may be performed outside of the MRI magnet in a stereotaxic intraoperative workspace or under the guidance of an alternative diagnostic imaging modality such as fluoroscopy, computed-assisted tomographic (CAT) scanner, or ultrasonography instrumentation.

In certain aspects, the disclosure provides a composition for image-guided treatment of a subject with a condition associated with an inflammatory response in an internal organ comprising a $^{19}$F MRI fluorocarbon imaging reagent.

In certain embodiments, the medicament is selected from a small molecule, protein, nucleic acid, or a cellular therapeutic. In certain embodiments, the medicament comprises stem cells. In certain embodiments, the medicament is administered by direct left ventricle injection (DLVI). In certain embodiments, the medicament is administered via a catheter. In certain embodiments, the medicament is administered endoscopically, with laparoscopic administration used in the abdominal cavity. In certain embodiments, the fluorocarbon imaging reagent comprises a perfluoropolyether. In certain embodiments, the fluorocarbon imaging reagent comprises perfluoroctylbromide (PFOB). In certain embodiments, the fluorocarbon imaging reagent is not taken up by non-phagocytic cells. In certain embodiments, the fluorocarbon imaging reagent is conjugated to an inflammatory cell targeting moiety. In certain embodiments, the fluorocarbon imaging reagent is formulated as an emulsion. In certain embodiments, the emulsion comprises particles having a mean diameter of between 30 and 500 nm. In certain embodiments, the fluorocarbon imaging reagent is cleared from the subject within a week.

In certain embodiments, the fluorocarbon comprises a perfluorinated polyether having an average formula:
1. XO(Y—O)$_n$Z
2. wherein Y is selected from the group consisting of:

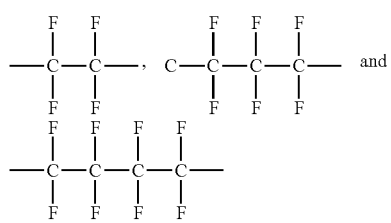 and 3. wherein n is an integer from 8 to 20; wherein X and Z are the same and are selected from the group consisting of perfluoroalkyls,
4. perfluoroethers, fluoroalkyls terminated with fluoroacyl, carboxyl, amide or ester, methylols, acid chlorides, amides, amidines, acrylates and esters.

In certain embodiments, the fluorocarbon imaging reagent comprises an additional functional moiety. In certain embodiments, the additional functional moiety is a detection moiety. In certain embodiments, the detection moiety is selected from the group consisting of: a fluorescent detection moiety and a PET detection moiety. In certain embodiments, said subject is a mammal. In certain embodiments, said mammal is a human. In certain embodiments, the steps of the method are performed in less than seven days. In certain embodiments, the steps of the method are performed in less than five days. In certain embodiments, the steps of the method are performed in less than four days.

Other aspects of the present disclosure will be apparent from the detailed description, examples and claims. The disclosure contemplates that any one or more of the foregoing aspects and embodiments of the disclosure can be combined with each other and/or with any of the embodiments or features provided below.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION

1. Overview

Figure 1:
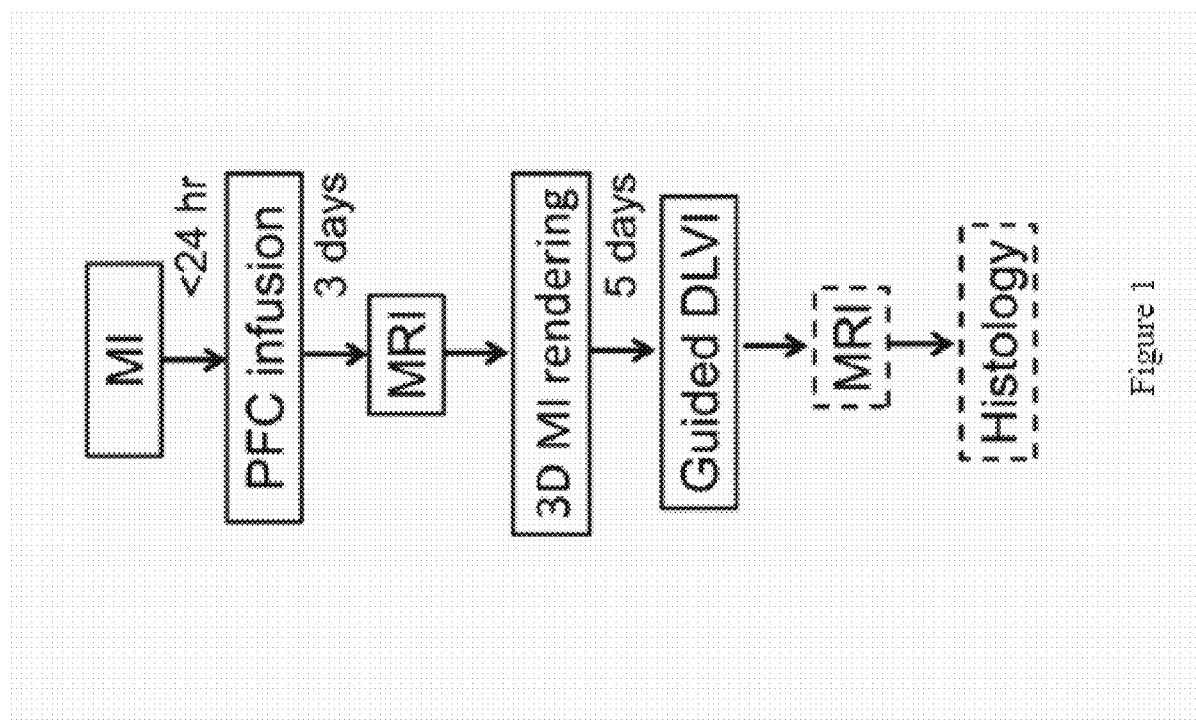
FIG. 1 shows an overview of an exemplary workflow. The dashed boxes are additional validation steps, extraneous to the clinical workflow.

There are many diseases, conditions and injuries associated with inflamed, injured or damaged internal organs that can be treated or diagnosed using the methods and compositions of the disclosure. Examples of internal organs include heart, kidney, bladder, liver, pancreas, intestine, appendix, esophagus, stomach, rectum, gall bladder, prostate, uterus, ovary, lung, brain, spinal cord, and spleen. Examples of diseases, conditions and injuries associated with inflamed, injured or damaged internal organs include myocardial infarction, cancer, ARDS, COPD, asthma, appendicitis, abdominal aortic aneurysm, atherosclerosis, autoimmune diseases, bacterial infection, celiac disease, cholecystitis, chronic prostatitis, diverticulitis, Crohn's disease, glomerulonephritis, graft versus host disease, hypersensitivities, inflammatory bowel disease, interstitial cystitis, pelvic inflammatory disease, occult infection, pancreatitis, kidney stones, reperfusion injury, rheumatoid arthritis, sarcoidosis, sepsis, transplant rejection, trauma, ulcerative colitis, vasculitis, and viral infection. As used herein, the term "condition associated with an inflammatory response" refers to any diseases, conditions and injuries associated with an inflamed, injured or damaged internal organ where there is an associated inflammatory response. As used herein, the term "affected tissue" refers to tissue that has a change or reaction (e.g., a physiological change or reaction) as a result of the condition associated with an inflammatory response. As used herein, the term "inflammatory response" refers to an immune response that includes the attraction of phagocytic immune cells to a tissue.

An example of a common disease associated with a condition associated with an inflammatory response in an internal organ is myocardial infarction (MI). MI results in permanent left ventricle (LV) scarring that causes diminished pump efficiency and, commonly, heart failure. Towards reduction or elimination of scarring, there is increasing interest in reparative biological materials that can be introduced into the affected region of the LV early after MI. Exemplary biological materials include proteins, nucleic acids and cells (e.g., cellular preparations or compositions, whether homogenous or heterogeneous). The most promising route for the delivery of future biological materials is direct LV injection (DLVI)—although other routes of delivery are certainly possible and contemplated. Thus far, the utility of DLVI has been hampered by the lack of methods for accurate spatial targeting of affected tissue. This has impeded clinical translation of promising materials. Given that inflammation is the key early response to the infarction insult, as well as to other organ damage caused by injury or disease, its location represents a promising spatial cue that can be used as a target for biological materials delivery.

In order to treat injured or diseased internal organs, biological materials (e.g., medicaments) must gain access to the injured internal organs, and in some instances at or near the boundary between affected and healthy tissue in the organ. In certain embodiments, delivery of the medicament to at or near the boundary is important for achieving the maximal therapeutic benefit. For example, treatments for MI may be most effective when they gain access to where the post-infarction inflammatory cascade is playing out. One method for achieving such access for MI is by direct left ventricle injection (DLVI) into infarcted tissue. To date, the clinical practice of DLVI has involved tissue targeting based on indirect measures of infarction. Examples include direct visualization of abnormal motion or tissue mottling and non-visual assessment of diminished tissue motion or electrical vigor. The imprecision inherent in such methods has been one of the most vexing technical hurdles that have slowed translation of promising biological materials to the bedside. A technique that accurately delineates the location of the cellular inflammatory processes in order to identify where to introduce the biological materials would be far preferable and represents a significant advance in patient care.

A second major hurdle in making DLVI of biological materials a mainstay of post-MI therapy has been the lack of infarct detection techniques that are in harmony with the standard clinical workflow. As used herein, the term "clinical workflow" refers to how the patient and the flow of clinical information interact with clinical providers and administered procedures. Heretofore, the DLVI procedures have been performed in patients undergoing open cardiac surgery (a tiny minority of early post-MI patients) or have utilized techniques that are time consuming, technically difficult and not suited for routine use. If a technique could be developed for DLVI of biological materials that is minimally invasive, accurate, technically straightforward and deployable in harmony with a routine clinical workflow, it would provide an essential stepping stone for establishing targeted administration of biological material(s) as a standard of post-MI care. Given the high annual incidence of MI, which will be sustained in the west and likely increase worldwide in the developing healthcare markets of China and India, the health impact of such technologies would be considerable. The present disclosure addresses this need and provides methods and compositions for accurately delivering medicaments to internal organs, such as to the boundary of affected and healthy tissue of an internal organ.

An inflammatory response in the heart triggered by MI is just one example of the applicability of the present disclosure. Numerous other diseases, condition and injuries of other organs could be suitably addressed using the methods described herein. By way of further non-limiting example, primary and/or metastatic tumors of internal organs result in a host of physiological changes in that organ, including an inflammatory response. Thus, the present disclosure is equally applicable to imaging cancers of internal organs for the purpose of improving therapeutic or diagnostic interventions.

In certain embodiments, the medicament is delivered to one or more affected tissue sites that are 1 cm, 9 mm, 8 mm, 7 mm, 6 mm, 5 mm, 4 mm, 3 mm, 2 mm, or 1 mm in size.

Thus, there is a great unmet need for inflammation-specific imaging tools, however, existing technologies have had very limited impact. There are several diagnostic imaging modalities routinely used in humans, including radio-isotope methods such as single photon emission coherent tomography (SPECT) and positive emission tomography (PET), MRI, computed tomography (CT), and ultrasound. Adopting existing diagnostic imaging modalities to yield high-resolution 3D images of inflammatory regions with high specificity is a complex problem. Effective inflammation visualization of injured internal organs will require innovative approaches in imaging agent design, data acquisition, and analysis algorithms. Only then will it be feasible to accurately diagnose or deliver medicaments to the boundary and/or surrounding regions of affected and healthy tissue of an internal organ or to a specific affected area.

Similarly, the ability to identify regions of inflammation and then use this information to direct a diagnostic procedure, such as a tissue biopsy, could greatly improve the ability of clinicians to characterize disease and injury in internal organs and tissues. As an example, organ transplant rejection is a major medical complication to solid organ transplant procedures. However, the inflammation associated with this condition is known to be very heterogeneous across the organ and this limits the overall robustness and clinical utility of invasive tissue biopsies because of sampling error due to imprecise knowledge about where to obtain the tissue bites used for histological and immunohistochemical analysis. PET and SPECT are highly sensitive in vivo, but have definite limitations for inflammation imaging. Generally, tracking labeled cells with radioactive tracers is challenging because of limited spatial resolution (10-12) and the limited half-life of radioisotopes that limits its utility in a clinically-relevant workflow. PET imaging using the F-18 fluorodeoxyglucose (18FDG) probe has been used for investigating MI inflammation in human studies by detecting metabolic activity (13,14); however, this approach has a high background and low spatial resolution. Thus, it requires an additional CT scan for anatomical localization. By themselves, CT or ultrasound does not have inflammation specificity needed to fulfill the clinical need.

Magnetic resonance imaging (MRI) has potential for delineation of internal organ inflammation because of its excellent soft tissue contrast and high spatial resolution. However, the inflammatory process associated with recent MI, for example, is rather indistinct in standard ($^1$H) images using endogenous contrast mechanisms (e.g., T1- or T2-weighted images), and thus inadequate to guide targeting. Efforts have been made to highlight inflammation using superparamagnetic iron-oxide (SPIO) nanoparticle contrast agents (15-19). When SPIO particles are introduced intravenously, they are taken up by phagocytic cells, including macrophages and monocytes. The SPIO-laden macrophages subsequently participate in the inflammatory process occurring in the infarcted region (15,20), yielding $^1$H image contrast in T2*-weighted images.

Although prior reports have demonstrated utility in SPIO cell tracking for cardiac applications, the technique has two key limitations that inhibit its clinical translation. First, in order to assay whether inflammation is present, it is often necessary to interpret subtle changes in grayscale contrast indicated SPIO deposits (i.e., labeled macrophages) reside, a task made difficult by the large $^1$H background signal from mobile water and substantial intrinsic tissue contrast. Thus, the SPIO technique would require scans prior to contrast injection to characterize the background contrast in regions of interest, effectively doubling the number of MRI scans needed, which is expensive and burdensome to the patient. Second, the SPIO reagent cannot be used to reliably assay the magnitude of inflammation (21). Possibly related to these limitations is that at present there are no SPIO imaging-specific agents approved for human use in the U.S. Thus, mapping inflammation after MI reliably using SPIO contrast agents is impractical as part of a routine clinical workflow for DLVI delivery or to guide diagnostic procedures such as tissue biopsy.

Figure 2:
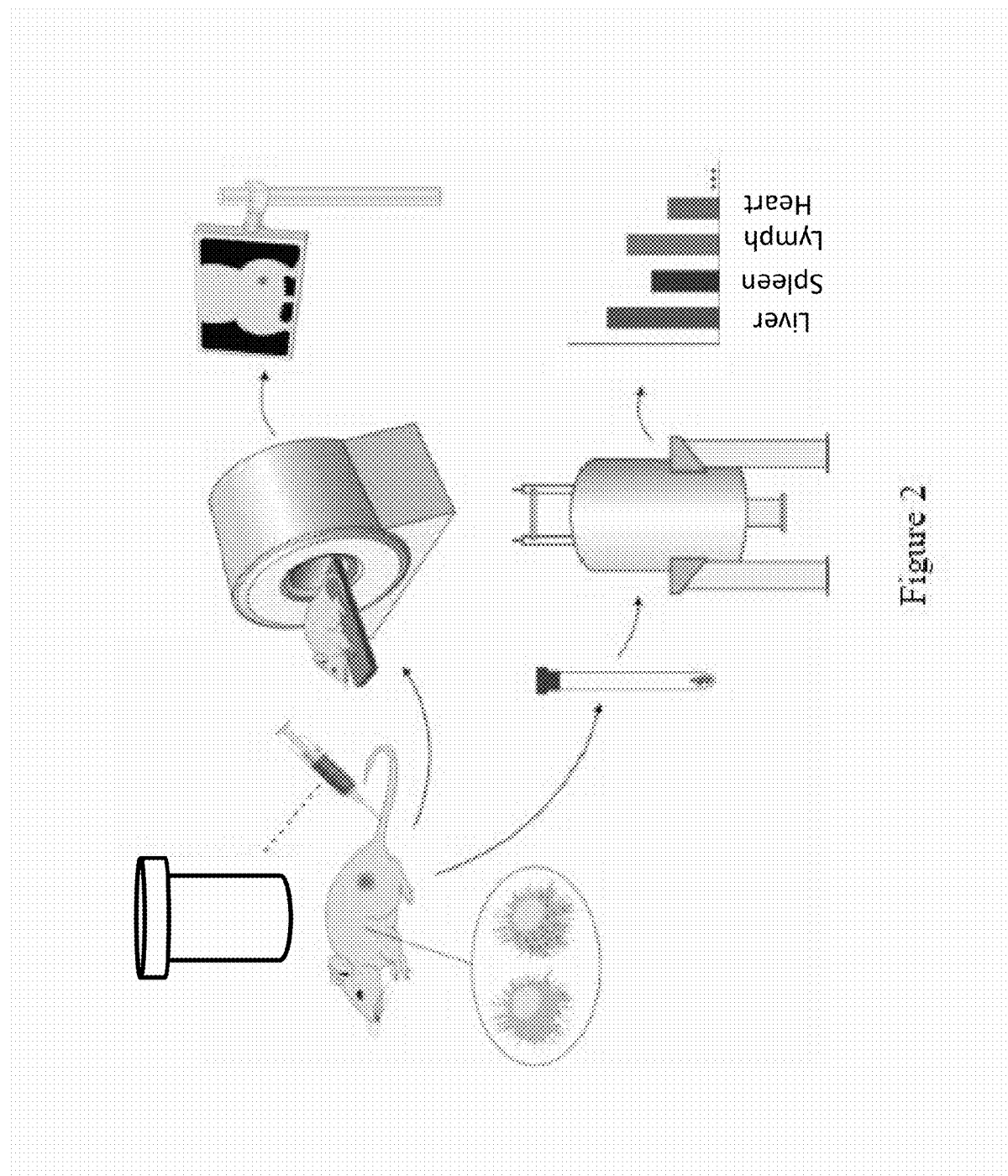
FIG. 2 depicts how perfluorocarbon (PFC) emulsion is used to detect and quantify inflammation in vivo. The emulsion labels inflammatory cells in vivo. Visualization and quantification of inflammation 'hot-spots' is performed using $^{19}$F MRI, and a conventional $^1$H image serves as an anatomical roadmap. Alternatively, NMR is used to sensitively and rapidly assay inflammation in intact tissues of interest.

The foregoing description provides examples of the shortcomings of current technology with respect to accurate imaging of inflammation of internal organs at a resolution suitable for application to therapeutic use. Perfluorocarbon (PFC) emulsion is a class of fluorine-based MRI 'tracer' agents (FIG. 2). The PFC emulsion contains tiny PFC droplets that are taken up by circulating macrophages and monocytes, and other cells of the reticuloendothelial system (RES), following administration. The fluorine-tagged macrophages participate in any inflammatory event in vivo. When labeled cells accumulate at sites of inflammation, they become detectable by $^{19}$F MRI. The key advantage of using $^{19}$F detection is that there is no background signal from the host's tissues and only labeled cells are detected. No manual image segmentation is required to display inflammatory regions. Quantification of the $^{19}$F signal yields an accurate marker of the degree of inflammation present. See U.S. Patent Application Publication No. 20070253910 which is hereby incorporated by reference in its entirety. PFC can be used to detect a wide range of lesions and diseases where inflammation is a hallmark. Most MRI scanners can be adapted to image $^{19}$F with the addition of a suitable $^{19}$F/$^{1}$H coil plug-in and other minor hardware/software modifications, and numerous vendors of aftermarket MRI coils can supply a $^{19}$F/$^{1}$H coil.

The low toxicity of PFC materials is well understood (22). The PFC emulsions have been rigorously tested and are biologically safe, presenting no observed adverse effects to viability or function in cells (23,24). Numerous studies have investigated the impact of PFC cell labeling on cellular phenotype and function in primary immune cells using a variety of sensitive in vitro assays, for example in the context of human dendritic cells (24,25) and murine T cells (26-28). In tissues, PFC accumulates in the reticuloendothelial system initially and is cleared via lung exhalation.

From ex vivo labeling studies, it has been shown that the minimum cell detection sensitivity for $^{19}$F cell tracking is of the order $10^4$ to $10^5$ cells per voxel for clinical MRI systems and $10^3$-$10^4$ cells per voxel for high-field animal scanners (25, 26, 29, 30). Experimental details, such as the image acquisition methods, magnetic field strength, and detector coil configuration determine the actual sensitivity for a particular study. Importantly, $^{19}$F cell tracking does not demand a high $^{19}$F signal-to-noise ratio (SNR). Because there is negligible $^{19}$F background, any $^{19}$F signal detected is from labeled cells. Unlike $^{1}$H anatomical imaging, where one relies on its high SNR to resolve detailed anatomy and organ definition, the $^{19}$F image only needs to display localized "pools" of cells at often low SNR, and the $^{1}$H overlay provides the detailed anatomical context.

Figure 3:
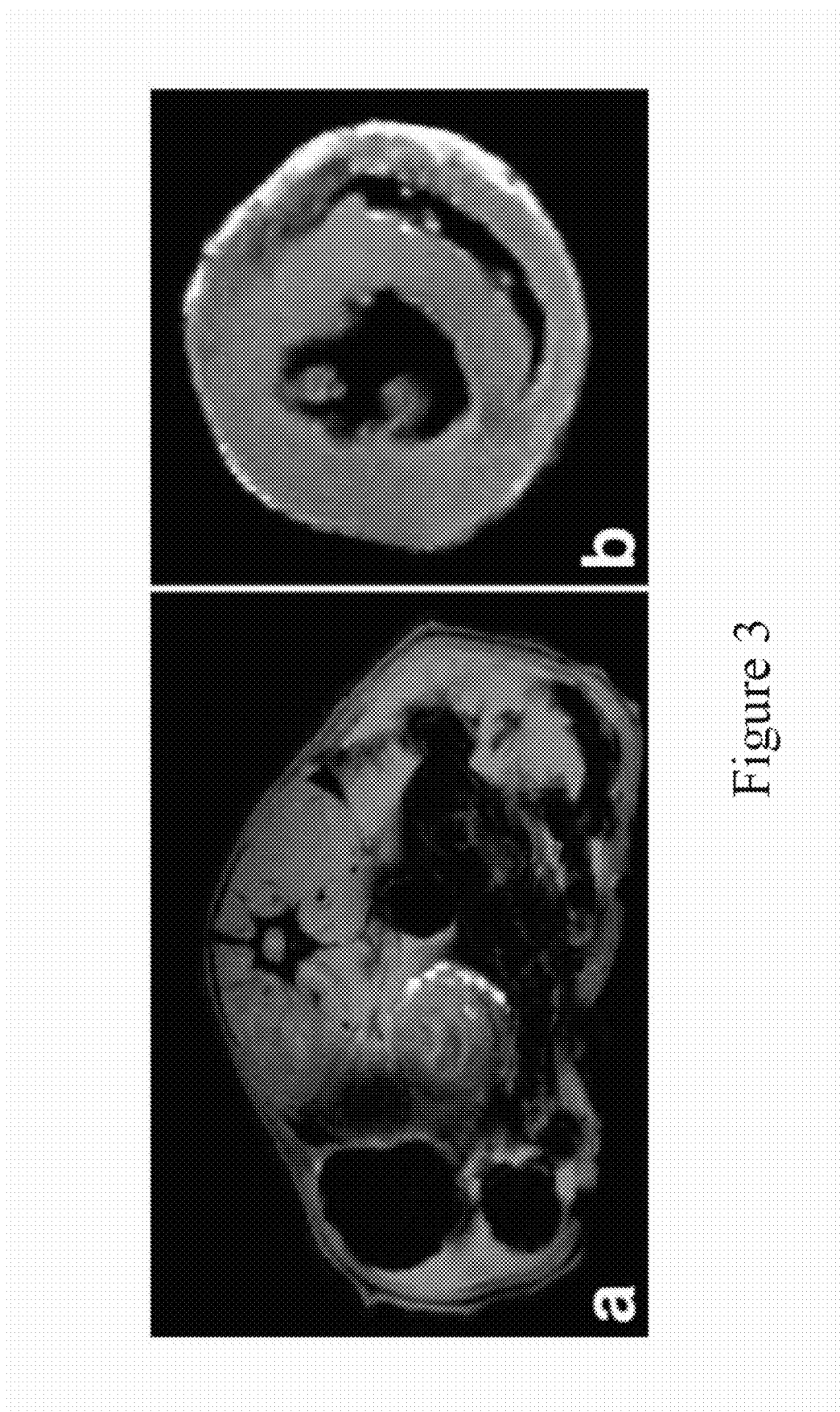
FIG. 3A-B shows PFC detection of macrophage infiltration in a heterotopic myocardium transplantation model. A working en bloc donor heart and lung from DA rat was transplanted to a recipient BN rat abdomen (day 0), leaving the native heart intact. At day 5, an i.v. injection of PFC was given, and 24 hours later a composite in vivo $^{19}$F/$^1$H image (panel a) displays macrophage infiltration in the allograft myocardium ($^{19}$F is 'hot-iron' pseudo-color). The native heart shows no $^{19}$F signal. Images were acquired in about 20 min at 7 T using a convention gradient-echo sequence. Panel (b): $^{19}$F signal in the myocardium was confirmed using high resolution ex vivo MRI of the fixed heart.
Figure 4:
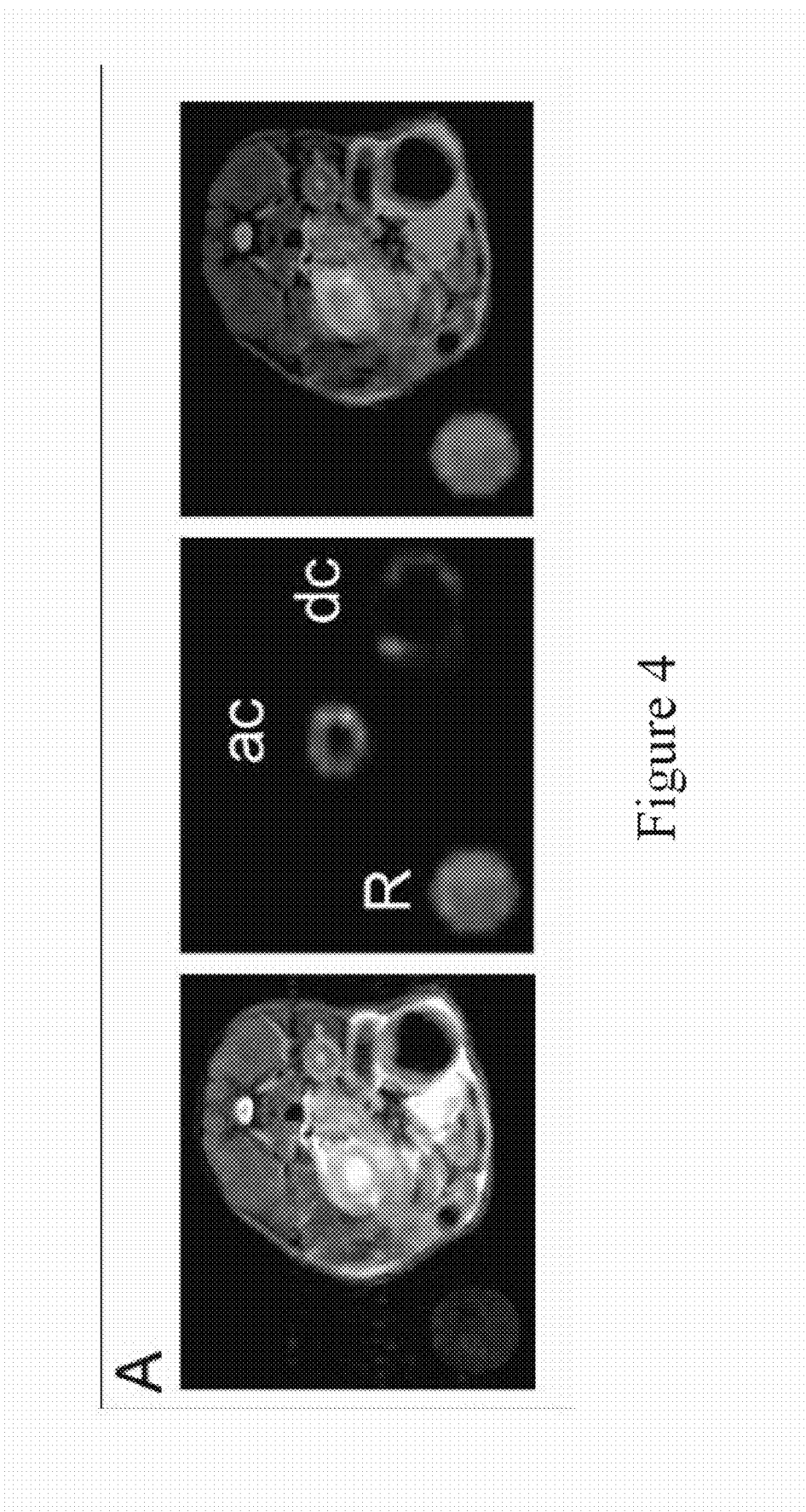
FIG. 4A-C shows visualization of inflammatory bowel disease (IBD) in an IL-10-/- mouse model using PFC emulsion and $^{19}$F MRI. The $^1$H/$^{19}$F MRI reveals PFC distribution in colon walls in a representative IBD mouse. (A) In vivo axial slices through the abdomen of a single mouse shows PFC accumulation in the ascending (ac) and descending colon (dc) in a mouse two days post-injection. The left panel shows $^1$H images (grayscale), the middle panel shows corresponding $^{19}$F images (pseudocolor), and the right panel shows composite $^1$H/$^{19}$F images. "R" represents a reference tube alongside the torso containing PFC emulsion. Panel (B) is a 3D rendering of the in vivo $^{19}$F MRI data from the abdomen in the IL-10−/− mice; substantial inflammation in the ascending and descending colon is apparent. Here, "ac"=ascending colon, "dc"=descending colon and "a"=anus. No manual image segmentation is used to make rendering, just noise thresholding of the $^{19}$F data. Panel (C) shows that macrophage burden forms the basis of $^{19}$F signal in the colon; data is immunohistochemistry of the colon in IL-10−/− mice and shows that PFC labeled with DiI (red) is localized within the macrophages (F4/80, green) at 2 days. Nuclei are stained with Hoechst 33342 (blue). The same study shows that PFC-DiI does not colocalize with lytic positive cells or endothelial cells.
Figure 4:
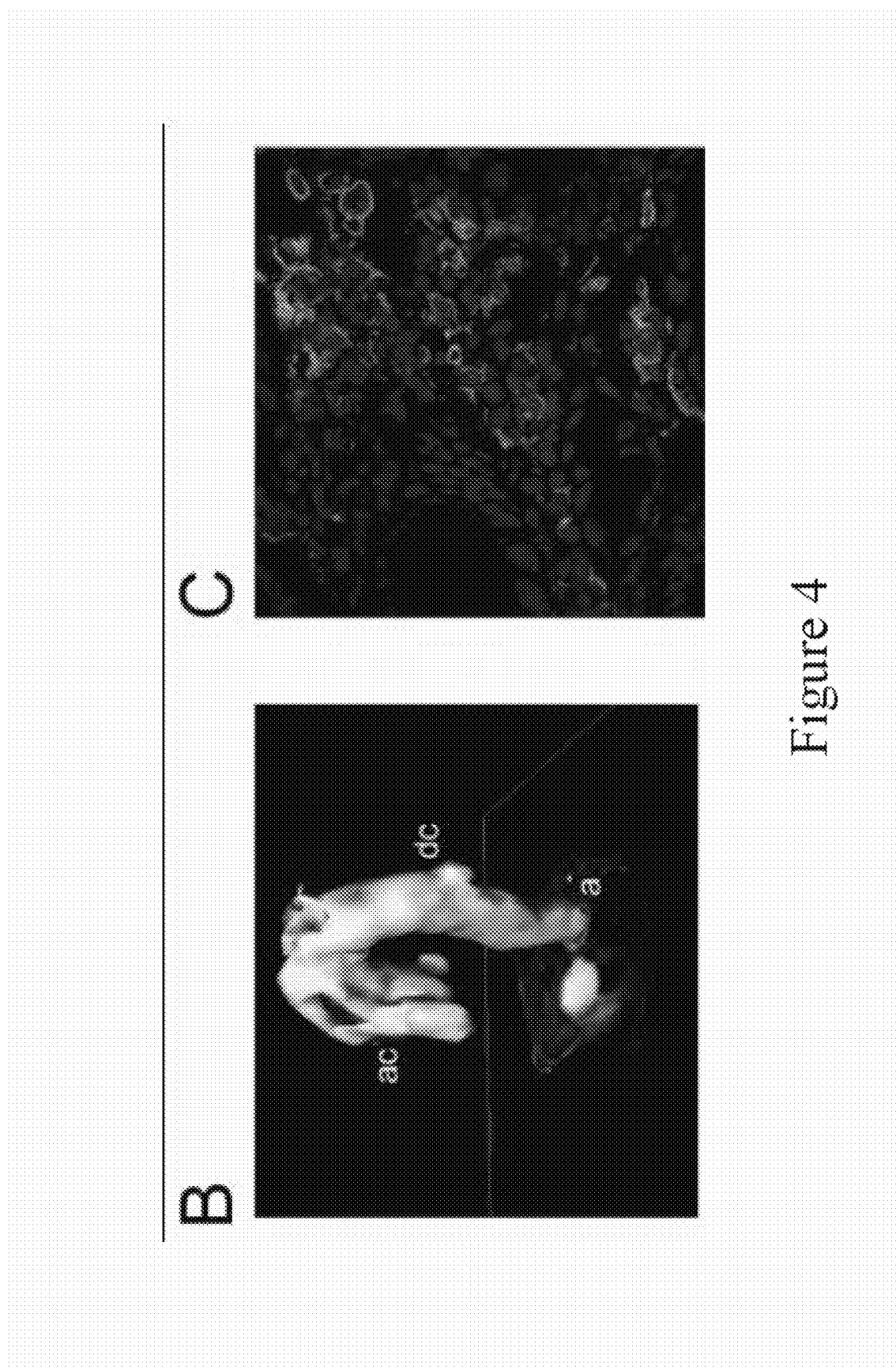

PFC emulsion can be used to assess inflammation in a wide range of disease models, for example, in myocardium transplant rejection (FIG. 3) (3), inflammatory bowel disease (FIG. 4) (6), multiple sclerosis (1), peripheral nerve inflammation (4), cerebral ischemia (5), and bacterial infection (2). Using detailed histological analyses, these studies also demonstrate that PFC labeling is virtually exclusive to macrophages within inflammatory lesions (e.g., FIG. 4). The $^{19}$F MRI signal can be readily quantified by integrating the signal in regions of interest, which is linearly proportional to the macrophage burden, as has been shown by quantitative, real-time PCR analysis (1).

The present disclosure describes the application of PFC MRI inflammation detection to image-guided treatment and diagnostic methods. PFC emulsions may be formulated for direct intravenous injection. Following injection, emulsion droplets are taken up by circulating inflammatory cells, particularly macrophages. These labeled macrophages participate in inflammatory events in the body, for example, in processes occurring in the infarcted region. An accumulation of labeled cells in the injured organ becomes detectable using MRI "tuned" to the fluorine-19 ($^{19}$F) contained in the PFC. A key advantage of $^{19}$F detection is that there is no background signal from the host's tissues and only labeled cells are detected. Three-dimensional (3D) images of the sites of inflammation can be obtained without manual segmentation, and quantification of the $^{19}$F signal correlates to the severity of the inflammatory lesion. Due to these advantages, $^{19}$F detection allows accurate diagnosis or delivery of a medicament or performance of a diagnostic procedure to internal organs, such as to the boundary between affected and healthy tissue in the organ or to a specific area of affected tissue. The ability to target areas of inflammation, including targeting at or near boundaries of affected and healthy tissue, is an important advance and likely critical for maximizing the benefits of numerous therapeutic treatments and diagnostics.

2. Imaging Reagents and Formulations

Imaging reagents for use in the disclosure are detectable in vivo. In certain embodiments, imaging reagents for use in the methods of the disclosure clear the subject within a few weeks; such as 1-3 weeks. In certain embodiments, imaging reagents for use in the methods of the disclosure clear the subject within a few days; such as 1-3 days. In certain embodiments, imaging reagents for use in the methods of the disclosure have a half-life of less than a few weeks; such as less than 1-3 weeks. In certain embodiments, imaging reagents for use in the methods of the disclosure have a half-life of less than a few days; such as less than 1-3 days.

In certain aspects, the imaging reagent used in the subject methods is a fluorocarbon, i.e., a molecule including at least one carbon-fluorine bond. By virtue of the $^{19}$F atoms, the imaging reagents disclosed herein may be detected by $^{19}$F MRI and other nuclear magnetic resonance techniques, such as magnetic resonance spectroscopy (MRS) techniques. In certain embodiments, a fluorocarbon imaging reagent will have one or more of the following properties: 1) tolerable cytotoxicity; 2) a $^{19}$F NMR spectrum that is simple, ideally having a single, narrow resonance to minimize chemical shift artifacts; 3) high sensitivity with a large number of NMR-equivalent fluorine atoms in each molecule; 4) formulated to permit in vivo labeling of inflammatory cells. In certain embodiments, a fluorocarbon imaging reagent will have 2, 3, or all 4 of these properties. Examples of suitable fluorocarbon imaging reagents have been described. See e.g., U.S. Patent Application Publication Nos. 2008/0292554, 2011/0110863 and 2009/0074673, which are hereby incorporated by reference in their entirety.

Exemplary compounds include aryl or heteroaryl trifluoromethyl sulfonic acid esters (triflates) or sulfonamides (triflamides), esters of fluorinated alcohols (such as 2,2,2-trifluoroethanol, perfluoro-tert-butanol, and 2,2,3,3,3-pentafluoropropanol), esters and amides of perfluoroalkanoic acids (such as trifluoroacetic acid, perfluorotetradecanoic acid, and nonafluoropentanoic acid), ethers of perfluoroalkanes, perfluoro-octyl-bromide (PFOB), structural analogs thereof, and derivatives thereof. Preferably, the imaging reagent comprises a plurality of fluorines bound to carbon, e.g., greater than 5, greater than 10, greater than 15 or greater than 20 fluorines bound to carbon. Preferably, at least 4, at least 8, at least 12 or at least 16 of the fluorines have a roughly equivalent NMR chemical shift. Typical emulsions are small particulates (~10-500 nm diameter) that are stable in aqueous solution and can be taken up by cells.

One of skill in the art will recognize that other fluorinated compounds will have desirable properties, particularly those fluorinate compounds in which each fluorine atom is in a similar chemical environment. Esters of perfluoro-tert-butanol, 1,3,5 tris(trifluoromethyl)benzene, hexafluoroacetone, poly(trifluoromethylethylene), and perfluorocyclohexane are examples of compounds having multiple fluorine atoms with $^{19}$F resonances that have the same, or nearly the same, Larmor frequencies. Accordingly, the foregoing are also exemplary of imaging reagents suitable for use in the subject methods.

In certain embodiments, the imaging reagent is a polymer. In certain embodiments, the imaging reagent is or includes a linear perfluoropolyether (linear PFPE), e.g., a compound having a structure or portion thereof comprising repeated units of —[O—CF$_2$(CF$_2$)$_x$CF$_2$]$_n$—, where x is an integer from 0 to 10, in some embodiments from 0-3, and n is an integer from 2 to 100, preferably from 4 to 40. Perfluorinated linear polyethylene oxide, for example, can be obtained from Exfluor Corp. (Round Rock, Tex.). Either or both ends (or a plurality of ends, in the case of branched polymers) may be derivatized with a moiety that provides an additional desired functionality. For example, an imaging reagent may have a formula of A-B-C, where A and/or C may be a functional moiety and B comprises repeated units of —[O—CF$_2$(CF$_2$)$_x$CF$_2$]$_n$—, where x is an integer from 0 to 10, in some embodiments from 0-3, and n is an integer from 2 to 100, and in some embodiments from 4 to 40. Functional moieties (e.g., non-fluorinated monomers conferring a particular desired function) are discussed further below.

A linear perfluoropolyether may also be described as a composition having the average formula:

XO(Y—O)$_n$Z wherein Y is selected from the group consisting of:

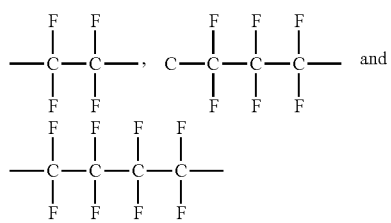

wherein n is an integer from 8 to 30; wherein X and Z are the same and are selected from the group consisting of perfluoroalkyls, perfluoroethers, fluoroalkyls terminated with fluoroacyl, carboxyl, amide or ester, methylols, acid chlorides, amides, amidines, acrylates and esters, as well as any of the preceding derivatized with a functional moiety.

While a completely fluorinated polymer can be formed, for example, by reacting a perfluorinated diacid with a perfluorinated dihalocarbon (such as 1,4-diiodooctafluorobutane), fluorinated monomers can be reacted with other monomers (optionally functional moieties, which may be non-fluorinated) to form hybrid polymers that are useful as imaging reagents. A variety of different non-fluorinated monomers can be used to vary the chemical and physical properties of the overall polymer, and make it possible to tailor the imaging reagent for specific uses. For example, a highly lipophilic imaging reagent may concentrate in adipocytes and other fatty tissues, while a highly hydrophilic imaging reagent may be useful for imaging the circulatory system or the lymph system.

Imaging reagents that may be suitable for use with the methods and uses of the disclosure have been described. See e.g., U.S. Patent Application Publication Nos. 2008/0292554, 2011/0110863 and 2009/0074673, which are hereby incorporated by reference in their entirety.

For labeling cells, the imaging reagents can be employed in one or more of at least three modalities: 1) imaging reagents that are internalized or otherwise absorbed by target cells without the formation of any covalent or other binding association; 2) imaging reagents that covalently attach to target cells; and 3) imaging reagents coupled to molecules, such as antibodies or ligands, that bind to molecules present on the target cells.

Imaging reagents of the first type include PFCs that are taken up by inflammatory cells and, preferably, are retained in the cell without degradation for a substantial period of time, e.g., having a half-life in the cell of at least 1 hour, at least 4 hours, at least about a day, at least about three days, or even at least about a week. For obvious reasons, the imaging reagent is selected so as to not interfere with ordinary cellular functions or exhibit cytotoxicity at the concentrations employed for labeling. Perfluoropolyethers show minimal toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See Means et al. (1990) Bioconjugate Chemistry 1:2-12, for additional approaches to such coupling.

Imaging reagents of the third type can be prepared by reacting imaging reagents with a functional moiety that is a cell-targeting ligand or antibody. Suitable ligands and antibodies can be selected for the application of interest. For example, a ligand that selectively targets hematopoietic cells could be labeled with an imaging reagent as described herein and administered to a patient, such as by injection.

Another PFC composition of interest is linear PFCs derivatized with a variety of end groups. The linear compounds have the advantage that one can conjugate a variety of functional entities to the end groups, such as functional moieties of various types. The $^{19}$F NMR spectra of these linear compounds generally is more complex than the macrocyclic compounds, but a PFC with two, three or four well-separated NMR signals can also be used. In this case it may be desirable to use an MRI pulse sequence that incorporates one or more off-resonance saturation pulses applied to the smaller resonance to eliminate any chemical shift artifacts within images, an approach that is well known in the art. A particularly useful application of linear PFCs is the synthesis of a "dual mode" agent that can be detected by $^{19}$F nuclear magnetic resonance techniques and includes a detection moiety that facilitates detection by a second detection method, such as PET or non-toxic fluorescent agents.

For example, detection moieties suitable for PET imaging may be used to create dual mode imaging reagents that are detectable by nuclear magnetic resonance techniques and by PET techniques. For example, the $^{18}$F isotope is a potent label for PET detection methods. A fluorocarbon imaging reagent may comprise a mixture of $^{18}$F and $^{19}$F isotopes, thus providing a dual mode label that is suitable for MRI/MRS and PET. $^{18}$F and $^{19}$F may also be added in separate monomers to form a mixed copolymer, or $^{18}$F portions may be located at either end of a linear polyether, at the position where most other functional moieties would be added. $^{18}$F has no NMR signal and so may be added at positions that would, for example, tend to decrease NMR linewidth, simplify the NMR spectrum, or alleviate chemical shifts from resonances that adversely affect the read-out obtained by a nuclear magnetic resonance technique. In addition, molecules of the fluorocarbon imaging reagents can incorporate other radioisotopes that are effective PET probes, such as $^{11}$C, $^{15}$O, and $^{13}$N. Those skilled in the art can, in view of this specification, devise many other PET-detectable moieties that can be incorporated into or, for example, attached to an endgroup(s), of the imaging reagents of this disclosure.

In certain embodiments, a linear perfluoropolyether may be derivatized with a relatively hydrophilic moiety at one, or preferably, both ends. For example, the hydrophilic moiety may be a polyethylene glycol, thus forming a tri-block copolymer with water-soluble regions on each end and a hydrophobic region in the center. When mixed in an aqueous environment, imaging reagents of this type will tend to form micelles, with the PFPE core surrounded by a water-soluble coat. Amino-PEG blocks are commercially available with a range of molecular weights. Coupling the PFPE core with other groups, such as aliphatic amines and phosphatidyl ethanolamine in place of the hydrophilic sections, will give derivatives with different solubility characteristics (see WO2005072780, which is hereby incorporated by reference in its entirety).

In certain embodiments, the disclosure provides formulations of imaging reagents that are suitable for uptake by cells. Emulsions comprising a fluorocarbon imaging reagent, such as a PFC, will preferably have a distribution of particle sizes that allow adequate cellular uptake. For example, it will generally be desirable that the mean particle size fall within a range from 10 nm to 500 nm, and more particularly within a range of from 30 nm to 150 nm or a range of from about 350 to 500 nm. In certain embodiments, the formulations will primarily be taken up by phagocytic cells. In certain embodiments, the formulations will not be taken up by non-phagocytic cells. Optionally, 25%, 50%, 75% or more of the particles will also fall within the selected range. Particle sizes may be evaluated by, for example, light scattering techniques or by visualizing the emulsion particles using EM micrographs. In certain cell types that have a relatively small amount of cytoplasm, such as most stem cells, particle sizes may be in the range of 10-50 nm in diameter. Emulsions for use in cells should preferably be stable at a wide range of temperatures. For example, it will often be desirable to store the emulsion at a cool temperature, in the range of 2-10° C., and particularly 4° C., and then warm the emulsion to room temperature (e.g., 18 to 28° C., and more typically 20 to 25° C.). Accordingly, a particular emulsion will retain the desired range of particle sizes at temperatures ranging from refrigeration temperatures up to body temperature. The surfactant may be designed to form stable emulsions that carry a large quantity of PFC into the aqueous phase. Additionally, it may have properties that increase the circulation time of the imaging reagent in the blood stream to provide adequate time for monocytes/macrophages to be strongly labeled in situ. Increasing the PFC intracellular loading improves sensitivity to the labeled cells. The efficiency of intracellular uptake depends on cell type. For example macrophages and dendritic cells will endocytose almost any particulate, whereas other cell types of interest may only be weakly phagocytic. In either case the uptake efficiency can be boosted by incorporating targeting peptides or by incorporating antibodies that target specific cell surface molecules.

The properties of an emulsion may be controlled primarily by the properties of the imaging reagent itself, the nature of surfactants and/or solvents used, and the processing used to generate the emulsion (e.g., sonication, etc.). Methods for forming PFC emulsions are extensively described in U.S. Pat. Nos. 5,330,681 and 4,990,283. A continuous phase of a polyhydroxylated compound, such as polyalcohols and saccharides in concentrated aqueous solution may be effective. The following polyalcohols and saccharides have proved to be particularly effective: glycerol, xylitol, mannitol, sorbitol, glucose, fructose, saccharose, maltitol, dimer compounds of glycerol (di-glycerol or bis(2,3-di-hydroxypropyl)ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and non-ionic surfactants. While thermodynamic equations may be used to attempt to predict mixtures of imaging reagents that will give emulsions having the desired particle sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

3. Nuclear Magnetic Resonance Techniques

As described herein, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of cell distributions. Following cell labeling, some portion of the subject, or the entire subject, may be examined by MRI to generate an MRI data set. A "data set", as the term is used herein, is intended to include raw data gathered during magnetic resonance probing of the subject material, as well as information processed, transformed or extracted from the raw data. Examples of processed information include two-dimensional or three-dimensional pictorial representations of the subject material. Another example of extracted information is a score representing the amount or concentration of imaging reagent or $^{19}$F signal in the subject material. For example, the signal-to-noise-ratio (SNR) of the $^{19}$F signal may be measured and used to calculate the abundance of labeled cells. This type of data may be gathered at a single region of the subject, such as, for example, the heart or another affected organ. Labeled cells may be examined in contexts other than in the subject.

In general, labeling agents of the disclosure are designed for use in conventional MRI detection systems. In the most common implementation of MRI, one observes the hydrogen nucleus (proton, $^1$H) in molecules of mobile water contained in subject materials. To detect labels disclosed herein, an alternate nucleus is detected, $^{19}$F. $^{19}$F MRI has only slightly less intrinsic sensitivity compared to $^1$H; the relative sensitivity is approximately 0.83. Both have a spin of ½. The natural isotopic abundance of $^{19}$F is 100%, which is comparable to 99.985% for $^1$H. The physical principles behind the detection and image formation are the same for both $^1$H and $^{19}$F MRI. The subject material is placed in a large static magnetic field. The field tends to align the magnetic moment associated with the $^1$H or $^{19}$F nuclei along the field direction. The nuclei are perturbed from equilibrium by pulsed radiofrequency (RF) radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed using a computer to yield images.

At constant magnetic field strength, the Larmor frequency of $^{19}$F is only slightly lower (~6%) compared to $^1$H. Thus, it is straightforward to adapt conventional MRI scanners, both hardware and software, to acquire $^{19}$F data. The $^{19}$F detection may be coupled with different types of magnetic resonance scans, such as MRI, MRS or other techniques. Typically, it will be desirable to obtain a $^1$H MRI image to compare against the $^{19}$F image. In a living organism or other biological tissue, the proton MRI will provide an image of the subject material and allow one to define the anatomical context of the labeled cells detected in the $^{19}$F image. In one embodiment of the disclosure, data is collected for both $^{19}$F and $^1$H during the same session; the subject is not moved during these acquisitions to better ensure that the two data sets are in spatial registration. Normally, $^{19}$F and $^1$H data sets are acquired sequentially, in either order. Alternatively, with appropriate modifications to the hardware and/or software of the MRI instrument, both data sets can be acquired simultaneously, for example, to conserve imaging time. Other imaging techniques, such as fluorescence or PET detection may be coupled with $^{19}$F MRI. This will be particularly desirable where a fluorocarbon imaging reagent has been derivatized with an additional imaging moiety.

MRI examination may be conducted according to any suitable methodology known in the art. Many different types of MRI pulse sequences—i.e., the set of instructions used by the MRI apparatus to orchestrate data collection, and signal processing techniques (e.g. Fourier transform and projection reconstruction)—have been developed over the years for collecting and processing image data (for example, see *Magnetic Resonance Imaging, Third Edition*, editors D. D. Stark and W. G. Bradley, Mosby, Inc., St. Louis Mo. 1999). The reagents and methods of this disclosure are not tied to any particular imaging pulse sequence or processing method of the raw NMR signals. For example, MRI methods that can be applied to this disclosure broadly encompasses spin-echo, stimulated-echo, gradient-echo, free-induction decay based imaging, and any combination thereof. Fast imaging techniques, where more than one line in k-space or large segments of k-space are acquired from each excited signal, are also highly suitable to acquire the $^{19}$F (or $^1$H) data. Examples of fast imaging techniques include fast spin-echo approaches (e.g., FSE, turbo SE, TSE, RARE, or HASTE), echo-planar imaging (EPI), combined gradient-echo and spin-echo techniques (e.g., GRASE), spiral imaging, and burst imaging. Additionally, emerging MRI methods have been studied that accelerate MRI data acquisition by not acquiring every line of k-space. Compressed sensing (CS) has been adapted from information theory as a generalizable tool to significantly reduce MRI acquisition time (see, e.g., U.S. Pat. Nos. 7,602,183, 7,659,718, 7,791,338 and 8,040,135, which are hereby incorporated herein by reference in their entireties). By exploiting the sparsity of objects to be imaged in a transformed domain, a small subset of conventional k-space measurements can be made to reconstruct the objects non-linearly. The artifacts caused by pseudo-randomized undersampling appear as incoherent noise. CS methods are particularly well-suited for $^{19}$F cell tracking and inflammation studies as the image data often display isolated, punctate signal distributions against a pure noise background in the image field of view; generally, the $^{19}$F signal of labeled cells appears as 'hot-spots' in MRI images that typically occupy of order 0.5-5% of the total image voxels, and thus CS is well suited for $^{19}$F cell tracking (See, Zhong et al. Magn. Reson. Med. July 2012, which is hereby incorporated by reference in its entirety). The development of new and improved pulse sequence and signal processing methods is a continuously evolving field, and persons skilled in the art can devise multiple ways to image the $^{19}$F labeled cells in their anatomical context.

As another example of a nuclear magnetic resonance technique, MRS can be used to detect the presence of fluorocarbon-labeled cells in localized tissues or organs. Normally MRS methods are implemented on a conventional MRI scanner. Often the localized volume of interest (VOI) is defined within a conventional anatomical $^1$H MRI scan. Subsequently the magnitude of the $^{19}$F NMR signal observed within the VOI is directly related to the number of labeled cells, and/or the inflammatory burden in the tissue or organ. Methods for isolating a VOI within a much larger subject are well known the art (for example, *Magnetic Resonance Imaging, Third Edition*, Chapter 9, Editors D. D. Stark and W. G. Bradley, Mosby, Inc., St. Louis Mo. 1999). Examples include using a localized RF surface coil near the VOL surface spoiling, surface coil $B_1$-gradient methods, slice-selective $B_0$-gradient techniques, STEAM, PRESS, image selective in vivo spectroscopy (ISIS), and magnetic resonance spectroscopic imaging (MRSI). The development of new and improved pulse sequence and signal processing methods is continuously evolving for MRS, and persons skilled in the art can devise multiple ways to detect the $^{19}$F NMR signals emanating from the fluorocarbon labeled cells in VOIs.

In certain aspects, these methods and uses involve administering to the individual an imaging reagent as described above in an amount sufficient to label inflammatory cells and imaging to identify boundaries between healthy and affected tissue or providing imaging data identifying boundaries between healthy and affected tissue in a subject who was previously administered an imaging reagent to label inflammatory cells. In certain embodiments, the imaging reagent is a $^{19}$F MRI fluorocarbon imaging reagent.

In certain embodiments, the internal organ is selected from the group consisting of heart, kidney, bladder, liver, pancreas, intestine, appendix, esophagus, stomach, rectum, gall bladder, prostate, uterus, ovary, lung, brain, spinal cord, or spleen. In certain embodiments, the condition associated with an inflammatory response in an internal organ is selected from the group consisting of myocardial infarction, cancer, ARDS, COPD, asthma, appendicitis, abdominal aortic aneurysm, atherosclerosis, autoimmune diseases, bacterial infection, celiac disease, cholecystitis, chronic prostatitis, diverticulitis, Crohn's disease, glomerulonephritis, graft versus host disease, hypersensitivities, inflammatory bowel disease, interstitial cystitis, pelvic inflammatory disease, occult infection, pancreatitis, kidney stones, reperfusion injury, rheumatoid arthritis, sarcoidosis, sepsis, transplant rejection, trauma, ulcerative colitis, vasculitis, and viral infection. In certain embodiments, the internal organ is the heart. In certain embodiments, the subject is in cardiac arrest or has had a myocardial infarction.

In certain embodiments, $^{19}$F MRI is used to generate an image of an affected internal organ. In certain embodiments, $^{1}$H MRI is used in conjunction with $^{19}$F MRI to image the anatomical underlay. In certain embodiments, $^{19}$F MRI is performed or analyzed only in a region of interest of the subject. In certain embodiments, $^{19}$F MRI is performed using compressed sensing (CS) methods. In certain embodiments, CS methods allow for enhanced cell detection and accelerated data acquisition.

In certain embodiments, $^{19}$F MRI can detect boundaries between healthy and affected tissue. In certain embodiments, $^{19}$F MRI can detect boundaries between healthy and affected tissue with enhanced resolution compared with other imaging methods. In certain embodiments, one or more boundaries between healthy and affected tissue is determined within 1 cm, 9 mm, 8 mm, 7 mm, 6 mm, 5 mm, 4 mm, 3 mm, 2 mm, or 1 mm of the actual boundary. In certain embodiments, the optimal delivery location is one or more affected tissue sites that are 1 cm, 9 mm, 8 mm, 7 mm, 6 mm, 5 mm, 4 mm, 3 mm, 2 mm, or 1 mm in size. In certain embodiments, the optimal delivery location is dependent on the organ, injury, disease or disorder and would be determined by the practitioner.

4. Image-Guided Treatment and Diagnostic Methods

In certain aspects, the present disclosure provides methods for image-guided treatment of a subject with a condition associated with an inflammatory response in an internal organ. In other aspects, the present disclosure provides methods for image-guided treatment of myocardial infarction (MI) in a subject. In certain aspects, the present disclosure provides uses of an imaging reagent for image-guiding the treatment of a subject with a condition associated with an inflammatory response in an internal organ. In certain aspects, the present disclosure provides a composition for image-guiding the treatment of a subject with a condition associated with an inflammatory response in an internal organ comprising an imaging reagent.

In certain aspects, the present disclosure provides methods for image-guided diagnosis of a subject with a condition associated with an inflammatory response in an internal organ. In certain embodiments, the treatment for use with the image-guided methods of the disclosure includes administration of anti-inflammatory formulations. In certain embodiments, the treatment for use with the image-guided methods of the disclosure results in organ repair activity. In certain embodiments, the treatment for use with the image-guided methods of the disclosure reduces, eliminates scarring and/or enhances tissue renewal. In certain aspects, the present disclosure provides methods for image-guided diagnosis via tissue biopsy that is subjected to further pathological analysis from an affected internal organ.

In certain aspects, these methods and uses involve administering to the individual an imaging reagent as described above in an amount sufficient to label inflammatory cells and imaging to identify boundaries between healthy and affected tissue or providing imaging data identifying boundaries between healthy and affected tissue in a subject who was previously administered an imaging reagent to label inflammatory cells. In certain embodiments, the imaging reagent is a $^{19}$F MRI fluorocarbon imaging reagent.

In certain aspects, the methods involve using the imaging reagent to label inflammatory cells ex vivo and administering the labeled cells to the subject. See, U.S. Pat. No. 8,147,806, which is hereby incorporated by reference in its entirety. Labeled inflammatory cells will home to sites of injury, damage or inflammation.

In certain embodiments, the internal organ is selected from the group consisting of heart, kidney, bladder, liver, pancreas, intestine, appendix, esophagus, stomach, rectum, gall bladder, lung, prostate, uterus, ovary, brain, spinal cord, or spleen. In certain embodiments, the condition associated with an inflammatory response in an internal organ is selected from the group consisting of myocardial infarction, cancer, ARDS, COPD, asthma, appendicitis, abdominal aortic aneurysm, atherosclerosis, autoimmune diseases, bacterial infection, celiac disease, cholecystitis, chronic prostatitis, diverticulitis, Crohn's disease, glomerulonephritis, graft versus host disease, hypersensitivities, inflammatory bowel disease, interstitial cystitis, pelvic inflammatory disease, occult infection, pancreatitis, kidney stones, reperfusion injury, rheumatoid arthritis, sarcoidosis, sepsis, transplant rejection, trauma, ulcerative colitis, vasculitis, and viral infection. In a particular embodiment, the internal organ is the heart. In certain embodiments, the subject is in cardiac arrest or has had a myocardial infarction.

In certain embodiments, $^{19}$F MRI is used to generate an image of the internal organ. In certain embodiments, $^{1}$H MRI is used in conjunction with $^{19}$F MRI to image the anatomical underlay. In certain embodiments, $^{19}$F MRI is performed or analyzed only in a region of interest of the subject. In certain embodiments, $^{19}$F MRI is performed using compressed censing (CS) methods.

In certain embodiments, the imaging dataset is used to make 3D images of inflammation and/or the affected tissue associated with the internal organ. In certain embodiments, the imaging dataset is used to make 3D images of MI-associated inflammation. In certain embodiments, the imaging dataset is used to make 3D images of the affected internal organ. In certain embodiments, the 3D dataset is volume-rendered. In certain embodiments, the data are analyzed quantitatively to measure the boundaries between healthy and affected tissue. In certain embodiments, the quantitative analysis improves the accuracy of the localization of the boundaries between healthy and affected tissue.

In certain embodiments, the 3D images of inflammation in the anatomical context are imported into a minimally invasive guided catheter-based delivery system for administering therapeutics and performing procedures stereotactically (see, e.g., U.S. Patent Application Publication No. 2004/0097805 and U.S. Pat. No. 6,470,207, which are hereby incorporated by reference in their entireties). Catheter navigation may be assisted by a commercial magnetic tracking system (e.g., NOGA™, Biosense Webster, Diamond Bar, Calif.) (42). The PFC cardiac image may be spatially registered to the operative field using the thoracic fiducial markers and commercial software (e.g., CartoMerge, Biosense). In certain embodiments, access to the LV endocardium for the DLVI catheter (e.g., MyoStar™, Biosense) may be achieved using a retrograde transaortic approach via femoral artery (45).

In certain aspects, these methods involve administering a medicament to treat the affected internal organ based on the roadmap, also referred to as a pattern, provided by the $^{19}$F MRI data. In certain embodiments, affected tissue and healthy tissue are heterogeneous throughout the organ. In certain embodiments, the medicament is administered at one or more sites at boundaries between healthy and affected tissue. In certain embodiments, the medicament is administered at one or more sites of affected tissue. In certain embodiments, the medicament is administered by direct left ventricle injection (DLVI). In certain embodiments, the medicament is administered via a catheter, such as an image catheter system.

In certain embodiments, the medicament is administered laproscopically. In certain embodiments, the medicament is administered using a conventional image-guided catheter delivery suite (e.g., Biosense Webster, Diamond Bar, Calif.) using the imported MRI-derived 3D inflammation images as a roadmap. In certain embodiments, the medicament is delivered to one or more boundaries between healthy and affected tissue within 1-10 mm of the actual boundary. In certain embodiments, the medicament is delivered to one or more affected tissue sites that are 1-10 mm in size. In certain embodiments, the optimal delivery location is dependent on the organ, injury, disease or disorder and would be known to one of skill in the art.

In certain embodiments, the image guided treatment or biopsy may be performed in situ in the MRI instrument using suitable non-magnetic, MRI-compatible surgical instruments for delivery of therapeutics or biopsy collection. In other embodiments, the image-guided treatment or biopsy may be performed outside of the MRI magnet in a stereotaxic intraoperative workspace or under the guidance of an alternative diagnostic imaging modality such as fluoroscopy, computed-assisted tomographic (CAT) scanner, or ultrasonography instrumentation.

In certain embodiments, the medicament is selected from a small molecule, protein, nucleic acid, or a cellular therapeutic. In certain embodiments, the medicament comprises stem cells. In certain embodiments, all of the steps of the method are performed in less than 7, 6, 5, 4, 3, 2 days or in a single day. In certain embodiments, the administration step is performed within one, two or three days of the MI or organ injury. In certain embodiments, the imaging step is performed within two, three, four or five days of the MI or organ injury. In certain embodiments, the treatment step is performed within 3, 4, 5, 6 or 7 days of the MI or organ injury. In certain embodiments, the treatment step is performed within 1, 2, 3, 4, 5, 6 or 7 days of the PFC administration.

In certain aspects, these methods involve guiding diagnostic procedures based on the roadmap provided by the $^{19}$F MRI data in order to diagnose the affected internal organ. In certain embodiments, the method for image-guided diagnosis of a subject with a condition associated with an inflammatory response in an internal organ comprises: administering a $^{19}$F MRI fluorocarbon imaging reagent to said subject to label inflammatory cells, performing $^{19}$F MRI of the subject to detect labeled inflammatory cells, identifying, for the internal organ, boundaries between healthy and affected tissue in the subject using the $^{19}$F MRI data, and performing a diagnostic procedure on the internal organ based on the boundary data.

In certain embodiments, the internal organ is selected from the group consisting of heart, kidney, bladder, liver, pancreas, intestine, appendix, esophagus, stomach, rectum, gall bladder, prostate, uterus, ovary, lung, brain, spinal cord, or spleen. In certain embodiments, the condition associated with an inflammatory response in an internal organ is selected from the group consisting of myocardial infarction, cancer, ARDS, COPD, asthma, appendicitis, abdominal aortic aneurysm, atherosclerosis, autoimmune diseases, bacterial infection, celiac disease, cholecystitis, chronic prostatitis, diverticulitis, Crohn's disease, glomerulonephritis, graft versus host disease, hypersensitivities, inflammatory bowel disease, interstitial cystitis, pelvic inflammatory disease, occult infection, pancreatitis, kidney stones, reperfusion injury, rheumatoid arthritis, sarcoidosis, sepsis, transplant rejection, trauma, ulcerative colitis, vasculitis, and viral infection. In certain embodiments the condition is cancer (e.g., a primary or metastatic tumor). In certain embodiments, the affected tissue and healthy tissue are heterogeneous throughout the organ. In certain embodiments, the disease is a kidney, colon or liver pathology (e.g. primary or metastatic malignancy, primary inflammatory disease). In certain embodiments, the diagnostic procedure is a biopsy. Methods and equipment for performing image-guided biopsies are known in the art (see PCT Publication Nos. WO2012098483, WO2010018536, and WO2002085216, which are hereby incorporated by reference in their entireties).

In certain aspects, the methods and uses of the disclosure are particularly aimed at therapeutic and prophylactic treatment or diagnosis of conditions associated with an inflammatory response in internal organs of animals, and more particularly, humans. One of ordinary skill in the art will be able to measure the effectiveness of the disclosed methods using known assays and assays disclosed in the specification such as measuring the level of inflammation or the function of the organ.

In certain aspects, the image-guided methods of the disclosure can be integrated into the clinically relevant workflow for treating a condition associated with an inflammatory response in an internal organ. For example, within 24 hours of presentation with MI, patients typically undergo pharmacological and/or mechanical therapies to recanalize the obstructed coronary artery in order to restore blood flow to the infarcted territory (revascularization). At about this same period after entering the hospital, the PFC agent may be administered to the patient. The PFC agent clears the blood stream and is taken up by macrophages that home to sites of inflammation in the affected internal organ within the next few days. $^{19}$F MRI may be performed after this period of macrophage homing using methods such as CS methods and/or in combination with $^1$H imaging of the region of interest or the entire patient. The MRI dataset may then be used to generate a 3D image of the organ and the borders of affected and healthy tissue. The MRI data may also be modeled of volume-rendered quantified to improve the accuracy or appearance of the images. At a time when the patient is ready for treatment, such as about 3-7 days after MI, the medicament may then be administered using the MRI-derived 3D inflammation images of the borders and distribution of affected and healthy tissue as a guide to the optimal delivery location while the patient is still hospitalized, for example on the fifth day after the MI. The medicament may be administered by, for example, direct left ventricle injection (DLVI), via a catheter or laproscopically. A similar procedure can be used for other injuries, diseases or conditions depending on the relevant clinical workflow. For example, for outpatient procedures, the steps could be timed to coincide with hospital visits. In some embodiments, the PFC agent may be delivered at an alternative facility remote from the MRI imaging facility.

5. Medicaments

A medicament of the disclosure may be any medicament that is beneficial in the treatment of a condition associated with an inflammatory response in an internal organ. In certain embodiments, medicaments for use with the image-guided methods of the disclosure have anti-inflammatory activity. In certain embodiments, medicaments for use with the image-guided methods of the disclosure have organ repair activity. In certain embodiments, medicaments for use with the image-guided methods of the disclosure reduce or eliminate scarring. In certain embodiments, such as when the condition is cancer, the medicament may be, for example, anti-proliferative, cytotoxic, or induce apoptosis. In certain aspects, the medicament is selected from a small molecule, protein, nucleic acid, or a cellular therapeutic. Examples of medicaments for MI include, Src family tyrosine kinase inhibitor, calcitonin gene related peptide, delta PKC isozyme-specific antagonist and an ephrin-A. See U.S. Patent Application Publication Nos. 2008/0200481, 2009/0023643, 2009/0318351 and 2012/0122789, respectively, which are hereby incorporated by reference in their entirety. Additional, polypeptides useful in the compositions and methods of the disclosure are listed in U.S. Patent Application Publication No. 2011/0044947, which is hereby incorporated by reference in its entirety.

Recombinant Nucleic Acids

In certain aspects, the medicament may be a recombinant nucleic acid encoding a therapeutic polypeptide. The nucleic acids may be single-stranded or double-stranded, DNA or RNA molecules. These nucleic acids are useful as therapeutic agents. For example, these nucleic acids are useful in making recombinant soluble polypeptides which are administered to a cell or an individual as therapeutics. Alternatively, these nucleic acids can be directly administered to a cell or an individual as therapeutics such as in gene therapy. Examples of proteins delivered by gene therapy for treatment of MI include Kit Ligand-2 and HSP70i. See Higuchi et al., Mol Ther. 2009 February; 17(2):262-8 and U.S. Patent Application Publication No. 2004/0132190, respectively, which are hereby incorporated by reference in their entirety.

In certain embodiments, the recombinant nucleic acids of the disclosure may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In certain embodiments, the expression vector contains a selectable marker gene to allow the selection of transformed host cells. Selectable marker genes are well known in the art and will vary with the host cell used.

In certain aspect of the disclosure, the nucleic acid may be provided in an expression vector comprising a nucleotide sequence encoding a polypeptide and operably linked to at least one regulatory sequence. Regulatory sequences are art-recognized and are selected to direct expression of the soluble polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a soluble polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This disclosure also pertains to a host cell transfected with a recombinant gene including a coding sequence for one or more of the soluble polypeptide. The host cell may be any prokaryotic or eukaryotic cell. For example, a soluble polypeptide of the disclosure may be expressed in bacterial cells such as *E. coli*, insect cells (e.g., using a baculovirus expression system), yeast, or mammalian cells. Other suitable host cells are known to those skilled in the art.

Methods for gene therapy are known in the art. See for example, U.S. Pat. No. 5,399,346 by Anderson et al., which is hereby incorporated by reference. The therapeutic gene can be any gene having clinical usefulness in a condition associated with an inflammatory response in an internal organ, such as a gene encoding a gene product or protein that is involved in disease prevention or treatment, or a gene having a cell regulatory effect that is involved in disease prevention or treatment. The gene products may substitute a defective or missing gene product, protein, or cell regulatory effect in the patient, thereby enabling prevention or treatment of a disease or condition in the patient.

Accordingly, the invention further provides a method of image-guided delivery of a therapeutic gene to a patient having a condition associated with an inflammatory response in an internal organ. The preparation may be modified by techniques that are generally known in the art. The gene may be inserted at the border of the affected tissue using any gene transfer procedure, for example, naked DNA incorporation, direct injection of DNA, receptor-mediated DNA uptake, retroviral-mediated transfection, viral-mediated transfection, non-viral transfection, lipid-mediated transfection, electrotransfer, electroporation, calcium phosphate-mediated transfection, microinjection or proteoliposomes, all of which may involve the use of gene therapy vectors. Other vectors can be used besides retroviral vectors, including those derived from DNA viruses and other RNA viruses. As should be apparent when using an RNA virus, such virus includes RNA that encodes the desired agent so that the cells that are transfected with such RNA virus art therefore provided with DNA encoding a therapeutic gene product. Methods for accomplishing introduction of genes into cells are well known in the art (see, for example, Ausubel, id.).

Therapeutic Proteins

In certain aspects, the medicament comprises proteins that have therapeutic effects on conditions associated with an inflammatory response in an internal organ. Examples of therapeutic proteins for MI include Kit Ligand-2, HSP70i, ephrin-A and calcitonin gene related peptide.

In certain aspects, the medicament comprises antibodies that have therapeutic effects on conditions associated with an inflammatory response in an internal organ. It is understood that antibodies may be polyclonal or monoclonal; intact or truncated, e.g., F(ab')2, Fab, Fv; xenogeneic, allogeneic, syngeneic, fully human or modified forms thereof, e.g., humanized, chimeric. Fully human antibodies may be selected from transgenic animals that express human immunoglobulin genes or assembled from recombinant libraries expressing antibody fragments. Examples of targets for antagonistic antibodies for the treatment of MI include Src family tyrosine kinase and delta PKC isozyme.

Antisense and RNAi

In certain aspects, the medicament is an isolated nucleic acid compound comprising at least a portion that hybridizes to a transcript under physiological conditions and decreases the expression of the transcript in a cell. Such nucleic acids may be used as antagonists, as described herein. The transcript may be any pre-splicing transcript (i.e., including introns), post-splicing transcript, as well as any splice variant.

Examples of categories of nucleic acid compounds include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. Examples of targets for antagonistic nucleic acid compounds for the treatment of MI include Src family tyrosine kinase and delta PKC isozyme.

In certain aspects, the medicament is a cellular therapeutic. In certain aspects of the disclosure, cellular therapeutics may be useful for the delivery of therapeutic proteins. See U.S. Patent Application Publication Nos. 2011/0236431 and 2008/0267921, which are hereby incorporated by reference in their entirety. In one embodiment, cells can be isolated, grown in quantity ex vivo and then implanted to produce and secrete soluble factors, which may be active either locally (e.g. enzymes, cytokines, and neurotransmitters) or at a distance (e.g. hormones and growth regulators).

In another aspect of the disclosure, cells may be administered to a patient in order to accomplish complex therapeutic purposes, such as reconstitution of tissues or organs or differentiate to replace damaged tissue. In certain embodiments, cellular therapeutics are not used to deliver therapeutic proteins. In certain embodiments, cellular therapeutics are administered to a patient in order to accomplish complex therapeutic purposes and are used to deliver therapeutic proteins.

Methods described herein may be used with a wide range of cells, including both prokaryotic and eukaryotic cells, and preferably mammalian cells. Technologies for cell preparation include cell culture, cloning, nuclear transfer, genetic modification and encapsulation.

A partial list of suitable mammalian cells includes: blood cells, myoblasts, bone marrow cells, peripheral blood cells, umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells) and stem cells. In certain embodiments, the cells to be used are a fractionated population of immune cells. Recognized subpopulations of immune cells include the lymphocytes, such as B lymphocytes (Fc receptors, MHC class II, CD19+, CD21+), helper T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dendritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (i.e., cells derived from a genetically different individual of the same species) are also contemplated. Autologous cardiac stem and/or progenitor cells, derived from patient biopsy, is another therapeutic cell source. See U.S. Patent Application Publication No. 20080267921 and Marban et al., Lancet. 2012 Mar. 10; 379 (9819): 895-904, which are hereby incorporated by reference in their entirety. Xenogeneic (i.e., derived from a different species than the recipient) cells, such as cells from transgenic pigs, may also be administered. When the donor cells are xenogeneic, the cells may be obtained from an individual of a species within the same order, more preferably the same superfamily or family (e.g., when the recipient is a human, the cells may be derived from a primate, for example a member of the superfamily Hominoidea). Cells may, where medically and ethically appropriate, be obtained from any stage of development of the donor individual, including prenatal (e.g., embryonic or fetal), infant (e.g., from birth to approximately three years of age in humans), child (e.g. from about three years of age to about 13 years of age in humans), adolescent (e.g., from about 13 years of age to about 18 years of age in humans), young adult (e.g., from about 18 years of age to about 35 years of age in humans), adult (from about 35 years of age to about 55 years of age in humans) or elderly (e.g., from about 55 years and beyond of age in humans).

In certain embodiments, the cells are stem cells. Examples of human embryonic stem cells include those available through the following suppliers: Arcos Bioscience, Inc., Foster City, Calif., CyThera, Inc., San Diego, Calif., BresaGen, Inc., Athens, Ga., ES Cell International, Melbourne, Australia, Geron Corporation, Menlo Park, Calif., Göteborg University, Göteborg, Sweden, Karolinska Institute, Stockholm, Sweden, Maria Biotech Co. Ltd.—Maria Infertility Hospital Medical Institute, Seoul, Korea, MizMedi Hospital—Seoul National University, Seoul, Korea, National Centre for Biological Sciences/Tata Institute of Fundamental Research, Bangalore, India, Pochon CHA University, Seoul, Korea, Reliance Life Sciences, Mumbai, India, Technion University, Haifa, Israel, University of California, San Francisco, Calif., and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 6,331,406; 6,090,622; 5,843,780; 2002/0045259; 2002/0068045, which are hereby incorporated by reference. In certain embodiments, the human ES cells are selected from the list of approved cell lines provided by the National Institutes of Health and accessible at http://escr.nih.gov. In certain embodiments, an embryonic stem cell line is selected from the group consisting of: the WA09 line obtained from Dr. J. Thomson (Univ. of Wisconsin) and the UC01 and UC06 lines, both on the current NIH registry.

In certain embodiments, the cells are cardiomyocyte lineage cells. For example, a medicament containing cardiomyocyte lineage cell aggregates or cells derived therefrom may be provided for treatment of a human or animal body, including formulations for cardiac therapy. Cardiomyocyte lineage cells may be administered to a patient in a method for reconstituting or supplementing contractile and/or pace-making activity in cardiac tissue (see US Patent Application No. 2006/0040389, 2005/0112104, 2005/0244384, which are hereby incorporated by reference in their entirety).

In accordance with the present disclosure, cardiomyocyte lineage cells are used to regenerate or repair striated cardiac muscle that has been damaged through disease or degeneration. The labeled cardiomyocyte lineage cells integrate with the healthy tissue of the recipient to replace the function of the dead or damaged cells, thereby regenerating the cardiac muscle as a whole. Cardiac muscle does not normally have reparative potential.

The cardiomyocyte lineage cells may be cardiomyocyte precursor cells, or differentiated cardiomyocytes. See U.S. Patent Application Publication No. 2008/0267921 and Marban et al., Lancet. 2012 Mar. 10; 379 (9819): 895-904, which are hereby incorporated by reference in their entirety. Differentiated cardiomyocytes include one or more of primary cardiomyocytes, nodal (pacemaker) cardiomyocytes; conduction cardiomyocytes; and working (contractile) cardiomyocytes, which may be of atrial or ventricular type. In certain embodiments, cells come from a muscle sample (or other sample) that contains muscle progenitor cells such as satellite cells (see US Patent Application No. 2005/0244384, which is hereby incorporated by reference). In certain embodiments, cells are mesenchymal stem cells (MSCs) (see US Patent Application No. 20050112104, which is hereby incorporated by reference).

A "cardiomyocyte precursor" is defined as a cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA4, NRx2.5, N-cadherin, β1-adrenoceptor (β1-AR), ANF, the MEF-2 family of transcription factors, creatine kinase MB (CK-MB), myoglobin, or atrial natriuretic factor (ANF).

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example, Published US Patent Applications 2003/0003574; 2002/0123143; 2002/0016002 and Gritti et al. 2002 J Neurosci 22(2):437-45), the spinal cord (see, for example, U.S. Pat. Nos. 6,361,996; 5,851,832) or a neuroendocrine lineage, such as the adrenal gland, pituitary gland or certain portions of the gut (see, for example, U.S. Pat. No. 6,171,610 and PC12 cells as described in Kimura et al. 1994 J. Biol. Chem. 269: 18961-67). In certain embodiments, a neural stem cell is obtained from a peripheral tissue or an easily healed tissue, thereby providing an autologous population of cells for transplant.

Hematopoietic or mesenchymal stem cells may be employed in certain disclosed methods. Recent studies suggest that marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et al., 2001, Cell 105: 369-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,763,197; 5,750,397; 5,716,827; 5,643,741; 5,061,620. Examples of mesenchymal stem cells include those described in U.S. Pat. Nos. 5,486,359; 5,827,735; 5,942,225; 5,972,703, those described in PCT publication nos. WO 00/53795; WO 00/02654; WO 98/20907, and those described in Pittenger et al. and Zhao et al., supra.

Stem cell lines may be derived from mammals, such as rodents (e.g. mouse or rat), primates (e.g. monkeys, chimpanzees or humans), pigs, and ruminants (e.g. cows, sheep and goats), and particularly from humans. In certain embodiments, stem cells are derived from an autologous source or an HLA-type matched source. For example, stem cells may be obtained from a subject in need of pancreatic hormone-producing cells (e.g. diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some embodiments, cells for administration to a human should be compliant with good tissue practice guidelines set by the U.S. Food and Drug Administration (FDA) or equivalent regulatory agency in another country. Methods to develop such a cell line may include donor testing, and avoidance of exposure to non-human cells and products. Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immuno affinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic particles via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

In certain aspects of the disclosure, cells, or a subpopulation thereof, may be labeled with an imaging reagent ex vivo prior to administration, thus allowing the monitoring of these cells in vivo. See, U.S. Pat. No. 8,147,806, which is incorporated by reference in its entirety. In vivo monitoring by a nuclear magnetic resonance technique may be useful, for example, to evaluate the viability of the administered cells. A doctor may tailor a dosing schedule depending on the degree to which labeled cells are detected in a patient after administration. In vivo monitoring may also be useful in determining whether therapeutic cells have localized to a desired location. In general, it will be possible to investigate correlations between the migration behavior of therapeutic cells in vivo, as well as the number and/or survivorship of therapeutic cells in vivo, and therapeutic outcomes. When such correlations have been established, the in vivo imaging of therapeutic cells may be used as a prognostic indicator that may be helpful in selecting the appropriate dosage, administration modes and additional therapeutic interventions that will benefit the patient. Certain imaging advances of the disclosure will benefit a broad range of cellular therapeutic strategies because these imaging methodologies will be able to detect when, where and if the therapeutic cells have been delivered to the desired targets in vivo.

In certain embodiments, cells are labeled by contacting the cells with an emulsion of the imaging reagent, such that the reagent is taken up by cells. Both phagocytic and non-phagocytic cells may be labeled by such a method. For example, both dendritic cells (phagocytic) and gliosarcoma cells (non-phagocytic) can be labeled by contacting the cells with an emulsion of the imaging reagent.

A variety of methods may be used to label therapeutic cells with imaging reagent. In general, cells will be placed in contact with imaging reagent such that the imaging reagent becomes associated with the cell. Conditions will often be standard cell culture conditions designed to maintain cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are highly phagocytic and data presented in other studies demonstrate that such cells, and other phagocytic cell types, are readily labeled. One study in the experimental allergic encephalomyelitis (EAE) animal model showed that monocytes, labeled in situ following a bolus injection of emulsified PFC, could be detected in the CNS using $^{19}$F MRI. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fluorocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies).

As another example, one could label therapeutic cells ex vivo with a fluorocarbon (see, U.S. Pat. No. 8,147,806, which is incorporated by reference in its entirety) having a different $^{19}$F chemical shift than the fluorocarbon reagent used to label in situ the macrophage/inflammation regions. One could then detect or image both the delivered cell transplant and the affected region in the organ/tissue using spectrally-resolved $^{19}$F MRI/MRS. In this way one could validate the delivery of the therapeutic cells to the affected region, or the boundary region between lesion and healthy tissue. Alternatively, the therapeutic transplanted cells could be labeled using a metal-ion-based contrast agent such as superparamagnetic iron-oxide nanoparticles and imaged using conventional relaxation-time-weighted $^{1}$H MRI. The inflammation is visualized separately using 19F MRI, as described herein, as a pre-interventional planning step. After cell transplant MRI could be used to validate delivery using a combined $^{1}$H and $^{19}$F cell tracking approach.

6. Delivery of Medicaments

In certain embodiments, the medicament of the present disclosure is formulated with a pharmaceutically acceptable carrier. The therapeutic agents can be administered alone or as a component of a pharmaceutical formulation (composition). The therapeutic agents may be formulated for administration in any convenient way for use in human or veterinary medicine. Wetting agents, emulsifiers and lubricants, such as sodium lauryl sulfate and magnesium stearate, as well as coloring agents, release agents, gels, matrices, coating agents, preservatives and antioxidants can also be present in the compositions.

Formulations of the subject therapeutic agents include those suitable for parenteral administration to the internal organ. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

The amount of active ingredient which can be combined with a carrier material to produce a single dosage form will generally be that amount of the compound which produces a therapeutic effect.

In certain embodiments, methods of preparing these formulations or compositions include combining another type of medicament and a carrier and, optionally, one or more accessory ingredients. The formulations may be prepared with a liquid carrier, or a finely divided solid carrier, or both, and then, if necessary, shaping the product.

Pharmaceutical compositions suitable for parenteral administration may comprise one or more therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In other embodiments, polypeptide therapeutic agents of the instant disclosure can be expressed within cells from eukaryotic promoters. For example, a soluble polypeptide can be expressed in eukaryotic cells from an appropriate vector. The vectors may be DNA plasmids or viral vectors. Viral vectors can be constructed based on, but not limited to, adeno-associated virus, retrovirus, adenovirus, or alphavirus. In certain embodiments, the vectors are stably introduced in and persist in target cells. Alternatively, viral vectors can be used that provide for transient expression. Such vectors can be repeatedly administered as necessary. Delivery of vectors encoding the subject polypeptide therapeutic agent can be by administration to target cells explanted from the patient followed by reintroduction into the patient, or by any other means that would allow for introduction into the desired target cell (for a review see Couture et al., 1996, TIG., 12, 510).

Various methods may be used for delivery of cellular therapeutics including injections and use of special devices to implant cells in various organs. The present disclosure is not tied to any particular delivery method. Cells may be inserted into a delivery device which facilitates introduction by injection or implantation into the subjects. Such delivery devices may include tubes, e.g., catheters, for injecting cells and fluids into the body of a recipient subject. In a particular embodiment, the tubes additionally have a needle, e.g., a syringe, through which the cells of the disclosure can be introduced into the subject at the boundary between healthy and affected tissue. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such carriers and diluents is well known in the art. The solution is preferably sterile and fluid. The solution may be stable under the conditions of manufacture and storage and preserved against the contaminating action of microorganisms such as bacteria and fungi through the use of, for example, parabens, chlorobutanol, phenol, ascorbic acid, thimerosal, and the like. Solutions for use with the disclosure may be prepared by incorporating cells as described herein in a pharmaceutically acceptable carrier or diluent and, as required, other ingredients enumerated above, followed by filtered sterilization.

The application will be more readily understood by reference to the following examples, which are included merely for purposes of illustration of certain aspects and embodiments of the present application, and are not intended to limit the application.

EXAMPLES

Example 1

Clinical DLVI Workflow

The clinically relevant workflow for image-guided DLVI of therapeutic biomaterials to treat MI is shown in FIG. 1. This workflow is used with a PFC imaging agent that can be used to make 3D images of MI-associated inflammation.

Under the current standard of care, within 24 hours of presentation with MI, patients typically undergo pharmacological and/or mechanical therapies to recanalize the obstructed coronary artery in order to restore blood flow to the infarcted territory (revascularization). Subsequent days are dedicated to recovery, including optimization of enteral medications that are helpful in resting the heart and maintaining patency of the recanalized vessels. In this setting, an exemplary optimum interval for DLVI is 3-7 days after the MI, while the patient is still hospitalized. In this setting, for example, PFC emulsion would be infused on the first hospital day, MRI on approximately the third hospital day, and DLVI on the fourth or fifth hospital day (see FIG. 1). Within 24 hours after MI, the PFC agent is infused intravenously into the patient. After an additional 3 days, PFC clears the blood stream and is taken up by macrophages that home to sites of inflammation in the myocardium. A 3D $^{19}$F and $^{1}$H MRI of the heart is then acquired. The 3D dataset, comprised of a co-registered $^{19}$F and $^{1}$H (anatomical underlay) images, are volume-rendered.

The therapeutic biomaterial is then subsequently administered using a conventional image-guided catheter delivery suite (Biosense Webster, Diamond Bar, Calif.) using the imported MRI-derived 3D inflammation images as a roadmap.

Overall, image-guided DLVI of therapeutic biomaterials to treat MI can be integrated into the current clinical workflow.

Example 2

In Situ Labeling of Macrophages Using PFC Emulsion

The following experiments utilized the V-Sense PFC emulsion (Celsense). The molecule is optimized for MRI applications (i.e., large number of NMR-equivalent $^{19}$F's and short T1/T2 ratio) and can be used with conventional, fast-imaging methodologies. The PFC is formulated into emulsion droplets, having a mean diameter ~150 nm. The blood half-life of the PFC used in this study is ~10 hours in rodents.

MI was induced in an adult swine by a transient catheterization of the left circumflex artery. Afterwards, PFC was infused intravenously. After 4 days, the swine was imaged using a Siemens 3 T clinical scanner with a 7 cm diameter $^{19}$F/$^{1}$H surface coil placed on the chest. FIG. 5A shows a composite $^{19}$F/$^{1}$H scan. For $^{19}$F, the imaging time was 4 minutes 16 seconds per slice packet. The $^{19}$F image signal-to-noise ratio was ~18. ($^{1}$H FLASH imaging parameters were: TR/TE=164/1.2 ms, averages=1, slice thickness=4 mm, FOV=34×24.4 cm2, matrix size=256×184. $^{19}$F FLASH imaging parameters were TR/TE=500/6 ms, averages=16, slice thickness=4 mm, FOV=34×34 cm2, matrix size=64× 32). FIG. 5B shows a rendering 3D MRI scan at 7 T (Bruker) of the same heart after being excised and fixed, where the $^{19}$F is in pseudo-color and the $^{1}$H is in grayscale.

This experiment demonstrated the feasibility of imaging MI inflammation with PFC using a clinical scanner using a clinically-realistic scan time.

Example 3

Optimization of $^{19}$F Image Acquisitions to Enhance Inflammation Detection

To date, $^{19}$F cell tracking studies have mostly used conventional pulse sequences (spin-echo, RARE, GRE, etc.) that do not exploit the unique characteristics of $^{19}$F-derived data. The $^{19}$F signal appears as isolated pools of signal from cell deposits against a background of pure noise. Generally, the image field of view contains only 'sparse' data with, at most, only a few percent of voxels containing signal. Additionally, the $^{19}$F spin-density weighted images are generally devoid of structural information, which is provided by the $^{1}$H image underlay, and has minimal high-frequency spatial components. Due to the modest SNR, long MRI scan times may be required using conventional pulse sequences that can hinder the use of $^{19}$F detection in regions of low-grade inflammation.

Figure 6:
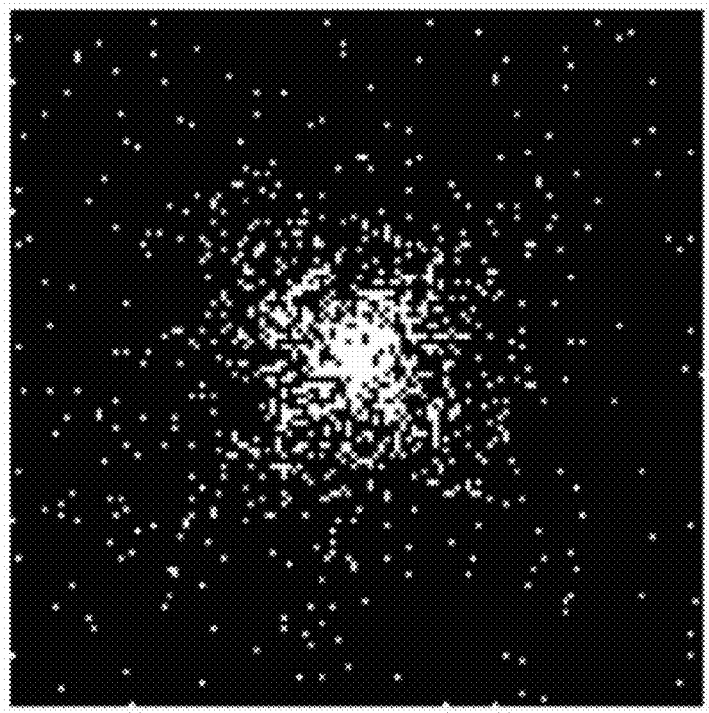
FIG. 6A-B shows pseudo-random compressed sensing (CS) undersampling schemes that emphasize the k-space center and greatly accelerate $^{19}$F MRI scans. Panel (a) is AF=4 and panel (b) is AF=16, where AF is acceleration factor. White pixels display sampling pattern. Undersampling occurs in the two phase encoding directions along the horizontal and vertical axes (matrix size 128×128), while in the readout direction the k-space remains fully sampled.
Figure 6:
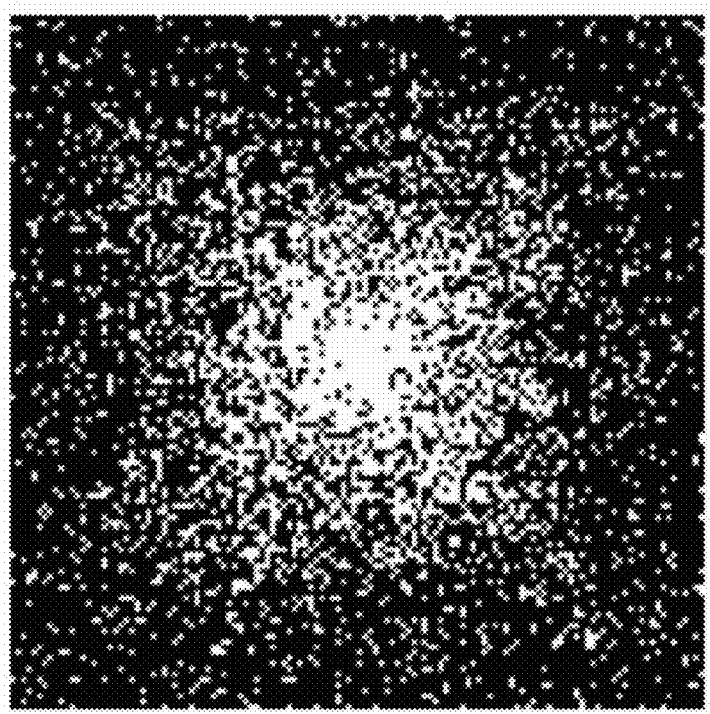

The compressed sensing (CS) methods (see, e.g., 31-36 and Zhong et al. Magn. Reson. Med. July 2012 and U.S. Pat. Nos. 7,602,183, 7,659,718, 7,791,338 and 8,040,135; each of the foregoing are incorporated herein by reference in their entirety) have been used to reduce MRI scan times in situations where images are expected to contain 'information-sparse' features. In CS, k-space is undersampled beyond the Nyquist criteria (FIGS. 6a and 6b) and image reconstruction constraints are customized for each application. CS is a 3D imaging approach that can improve the image SNR per unit acquisition time and therefore enhance the ability of $^{19}$F cell tracking to detect sparse macrophage numbers by enabling increased signal averaging within the temporal confines of a clinical scan.

Figure 7:
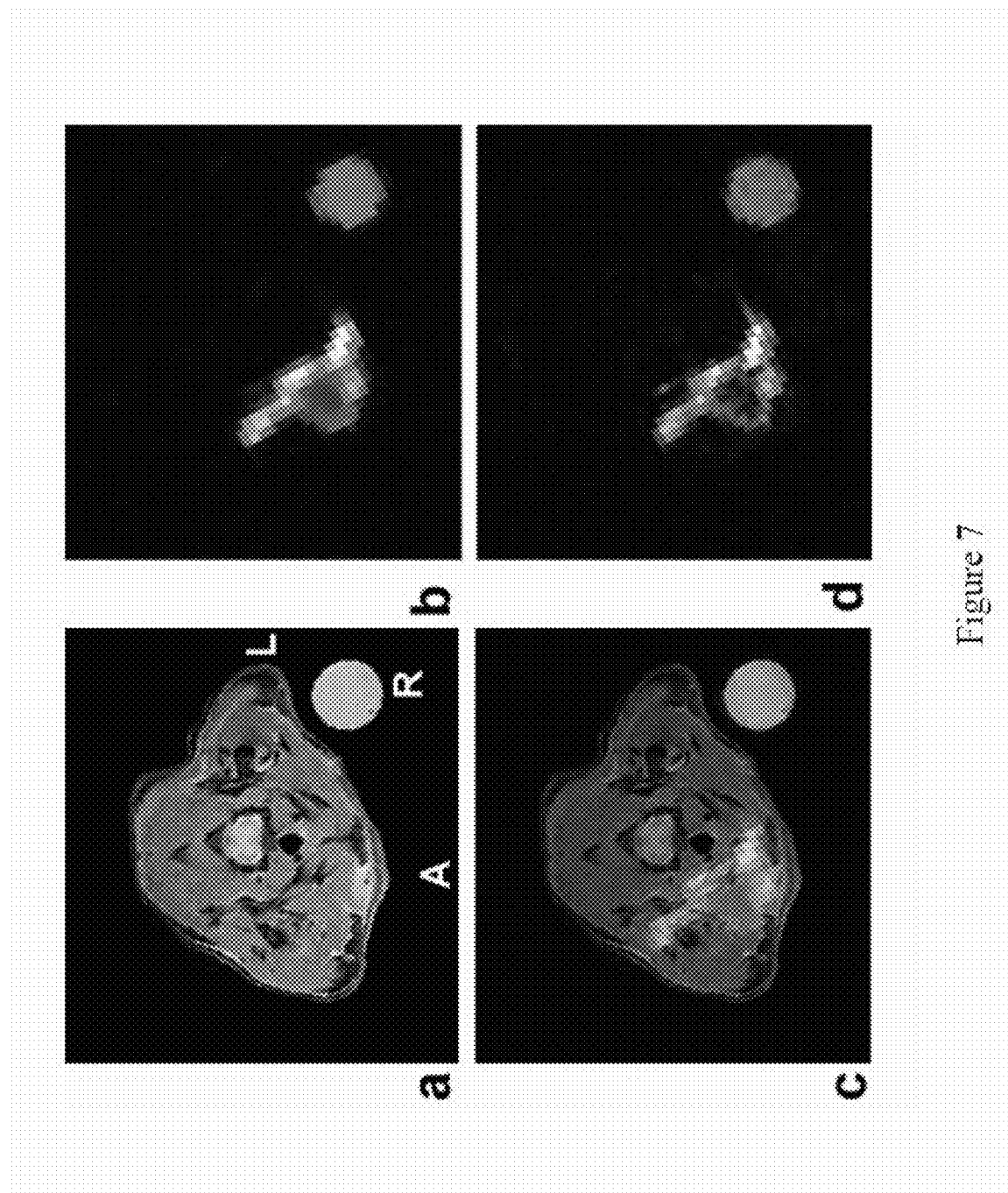
FIG. 7A-D show in vivo $^{19}$F 3D CS-RARE images in a mouse model of localized inflammation and the very rapid data acquisition acceleration afforded by the CS method for visualizing inflammation. The pseudo-colored images show macrophage (PFC) accumulation in the region of wounding-induced inflammation. Panel (a) shows a T2-weighted anatomical $^1$H image. Panel (b) is a single slice from a 3D $^{19}$F CS-RARE image with AF=8, and (c) is a $^1$H/$^{19}$F fused image of (a+b). Panel (d) is an AF=1 (fully-sampled k-space) RARE image. The PFC emulsion (V-Sense, Celsense, Inc.) was injected 24 hours after injury and imaged at 72 hours. Here, A=anterior wall, L=left, and R=reference.

It was demonstrated that CS is effective in significantly reducing the image acquisition time by at least 8-fold without seriously effecting image features and $^{19}$F spin quantification (See, Zhong et al. Magn. Reson. Med. July 2012, hereby incorporated by reference in its entirety). FIGS. 7a and 7c shows representative $^{1}$H/$^{19}$F images acquired on a Bruker 7 T scanner in a mouse model of localized inflammation induced by wounding. Inflammation is observed at the right anterior side of the animal proximal to the jugular vein (FIG. 7c). The $^{19}$F signal indicates the presence of phagocytic macrophages at the surgical site. With an 8-fold decrease in k-space sampling with CS, the $^{19}$F imaging time was <9 minutes yielding a high SNR image (~21.9). No significant blurring in the $^{19}$F feature was detected at the edge of the lesion or external reference capillary when compared to the conventional RARE image (FIGS. 7b,d). The de-noising effect by CS reconstruction was also observed (FIGS. 7b,d). With aid of the external PFC capillary in the image field of view, the total number of $^{19}$F spins observed in the lesion in vivo was analyzed and is proportional to the macrophage burden (1). The spin quantification was in close agreement, differing by only ~6% between the two k-space sampling patterns.

This experiment is expected to demonstrate that the implementation of CS methods on a clinical scanner will improve overall image quality and ensure clinically realistic scan times for $^{19}$F inflammation detection.

Example 4

Rodent Studies of MI

The timing of the proposed clinical workflow (FIG. 1) will be evaluated in a rodent species. A rat model of MI will be used to optimize PFC delivery parameters, including administration timing post-MI and the dose per body weight in order to best visualize inflammation via $^{19}$F MRI. The PFC-labeled macrophage persistence in the inflammatory lesions will be longitudinally characterized. The impact of the timing of PFC infusion, post-MI, on the $^{19}$F MRI detection efficacy will be determined.

Rodent MI Model—

Female Fisher 344 rats (n=15 total), 6 weeks of age, will be sourced from Harlan Laboratory (Indianapolis, Ind.). The induction of the MI rat model will be performed at the central vivarium. MI will be induced by a modified method of Patten et al. (39). Briefly, rats will be anesthetized with intraperitoneal ketamine (80 µg/g body weight) and xylazine (12 µg/g body weight) and the heart approached via a left thoracotomy. The pericardium will be stripped, and the left coronary artery will be ligated 100% at the tip of the left atrium. The infarction is made more extensive by gentle traction on the ligature to further expose the left coronary artery and placement of a second, more proximal ligature.

Animal Groups—

3 groups with N=5 animals per group will be used. The PFC emulsion will be injected via tail vein at differing times post-surgery in the different groups, where Groups 1, 2, and 3 will receive PFC at 0 (i.e., immediately after MI surgery), 24, and 48 hours, respectively. All animals will be injected with 2.8 ml/kg PFC emulsion, a relatively large dose that has been shown to be effective in other rat models (3).

MRI—

MRI data in rats will be acquired 72 hours after PFC infusion for all Groups. The blood half-life of the PFC emulsion is ~9.4 hours in rat (3), thus by 72 hours the reagent will essentially be cleared from the bloodstream and will have entered into the RES. Data will be acquired using a Bruker 7 T imaging system and cardiac imaging methods similar to those described elsewhere (3). A birdcage volume coil will be used that can be tuned to either $^{19}F$ or $^{1}H$. A calibrated $^{19}F$ reference standard containing dilute PFC emulsion in a capillary tube will be positioned alongside the animal's torso. The rats will be anesthetized using 2% Isoflurane in 70% O2 and 30% N2O. A potential $^{19}F$ signal in the heart from the Isoflurane will be insignificant compared to the macrophage-associated $^{19}F$. Animal temperature will be maintained at 37° C. during the course of the experiments. 3D T2-weighted $^{1}H$ cardiac images will be acquired using conventional cardio-respiratory gated RARE methods. To localize the myocardial inflammation, spin-density weighted $^{19}F$ images will be acquired using cardio-respiratory gated RARE with compressed sensing sampling (AF=8, see FIG. 7). The 3D $^{19}F$ images will be volume rendered in pseudo-color and superimposed onto the $^{1}H$ image using Amira software (Visage Imaging, Inc., San Diego, Calif.). The apparent inflammatory burden in the myocardium in each animal will be analyzed using Voxel Tracker™ software (Celsense). This program will be used to tabulate the total number of apparent $^{19}F$ spins in the 3D myocardium. Built-in tools allow one to define regions of interest (ROI) slice-by-slice in the heart, and the program calculates the total spins in ROI; an ROI in the reference tube of known $^{19}F$ concentration is used in this analysis. The software also calculates an error in the spin count using statistics that takes into account parameters such as the image SNR, etc. Among the different Groups (1 through 3) the trend of PFC uptake in the myocardium versus PFC injection timing post-MI will be empirically determined. Group averages of the $^{19}F$-apparent MI inflammation burden will be calculated along with the standard deviation. At the experimental endpoints the animals will sacrificed and the hearts removed, fixed, and stored.

Example 5

Dose Escalation

PFC dose escalation studies in the rat MI model will be performed to assess the minimum dose needed to reliably detect the MI-induced inflammation.

Animal Groups—

3 groups with N=5 animals per group will be used. The PFC emulsion will be injected via tail vein immediately after MI induction. Groups 1, 2, and 3 will receive PFC at 2.8, 1.4, and 0.7 ml/kg body weight, respectively.

Methods—

The identical rat model, MRI methods, and image quantification methods will be used as described above. All animals will be imaged at 72 hours after PFC infusion. We will qualitatively assess whether a similar inflammation distribution in the myocardium is observed, quantitate the SNR in inflammation 'hot-spots', and calculate group averages of the $^{19}F$-apparent MI inflammation burden (using Voxel Tracker™ as described above) and standard deviations.

This experiment is expected to provide data to assess the minimum dose needed to reliably detect the MI-induced inflammation.

Example 6

Longitudinal Monitoring of $^{19}F$ Persistence

The persistence of the $^{19}F$ signal in MI-induced inflammatory lesions over time will be assessed.

Animal Groups—

A single cohort of rats (N=5) will be used. The PFC emulsion will be injected via tail vein immediately after MI induction at a dose of 2.8 ml/kg body weight.

Methods—

All rats will be longitudinally imaged using the MRI methods described above. Imaging will be performed at 1, 2, 4 and 8 days after PFC infusion. The trend of PFC retention in the myocardium versus time after PFC infusion will be measured. For each time point, averages of the $^{19}F$-apparent MI inflammation burden will be calculated (using Voxel Tracker™) along with the standard deviation.

The design of the putative clinical workflow is shown in FIG. 1. These results will be used to validate the porcine studies as to: (i) the effective time window for PFC delivery post-MI, (ii) the minimum PFC dose that can be delivered to the animals to yield reliable detection of MI by $^{19}F$ MRI, and (iii) the maximum MRI observation time after PFC infusion.

It is expected that the PFC will be able to label MI lesions at all time-points studied, but to varying degrees. At the earliest PFC infusion time (i.e., 0 hours), the PFC labeled cells may contain significant contributions from phagocytic neutrophils in addition to macrophages, as would be expected in the earliest influx of inflammatory infiltrates. As with PFC emulsion in the IBD model (6) (see FIG. 4), the PFC and MI lesion should be observable even at 8 days.

Example 7

Generation of 3D PFC-Enhanced Images of the Myocardium

MI-associated inflammation will be labeled with PFC in situ, and the 3D inflammation pattern will be imaged using a clinical scanner and optimized MRI methods.

Porcine MI Model and PFC Delivery—

N=10 female wild-type pigs (35-45 kg) will be used. Via right femoral artery, a coronary fluoroscopy-guiding catheter will be positioned into the left main coronary artery ostium. Injection of dye will be performed to confirm a right coronary artery-dominant circulation; non right-dominant animals will be excluded. A balloon catheter will be advanced into the circumflex artery and inflated for 30 minutes. Twelve hours after deflation, a bolus of PFC will be slowly administered over ~30 min via a peripheral vein; the PFC volume will be indexed for body weight and based on the results of the rodent studies in Example 5. The swine will then be recovered and monitored.

MRI of MI Inflammation—

On post-MI day 3, animals will be brought into the MRI suite for scanning to visualize the MI-associated inflammation. The swine will be sedated using ketamine, undergo endotracheal intubation, placed on a mechanical ventilator, and Isoflurane in air inhalation gas will be delivered for the duration of the scan. Past experience has shown that the fluorine in Isoflurane does not accumulate in heart tissue.

Five fiducial markers (vitamin E capsules) will be placed on the thorax (three midline, two lateral) at predetermined locations to define a coordinate frame of reference. Cardiac electrodes will also be placed on the swine for cardiac-gated MRI acquisitions, and a $^{19}F$ capillary referenced will be placed alongside the torso for post-imaging quantification. The swine will be scanned using a 3 T Siemens Tim Trio, where a custom-built $^{19}F/^{1}H$ cardiac chest coil (Stark Contrast, Inc., Erlangen, Germany) placed on the torso will be used for transmit and receive. The imaging protocol will begin with the acquisition of a set of $^{1}H$-based localizers to confirm that the placement of the coil is optimal for the acquisition of the $^{19}F$ signals. Compressed sensing (AF=8, estimated 4 minutes acquisition time) will be used and incorporated into a RARE or gradient-echo sequence as a means to speed up the acquisition by taking advantage of the sparse nature of the $^{19}F$ signal in the myocardium. This will be achieved through random undersampling along the trajectories in conjunction with a random schedule of skipped trajectories on both angular directions. All image reconstruction will be performed online using customized versions of the software ported onto the Image Calculation Environment (ICE) of the scanner. Using the 3D visualization software Amira, the $^{19}F$ and $^{1}H$ data sets will be volume rendered and merged to obtain a 3D model of the inflammation hot-spots in the context of the myocardial anatomy, and the results will be stored as a DICOM file; this file will be used for the DLVI procedures.

This experiment will produce 3D inflammation patterns showing regions of inflammation, including MI border zones, in the heart.

Example 8

Demonstrate Accuracy of DLVI Guided by the PFC-Enhanced $^{19}F$ Images

Image-Guided DLVI—

On post-MI day 5, animals will be brought to the clinical interventional cardiology suite. DLVI catheter navigation will be assisted by a commercial magnetic tracking system (NOGA™, Biosense Webster, Diamond Bar, Calif.) (42). The PFC cardiac image will be spatially registered to the operative field using the thoracic fiducial markers and commercial software (CartoMerge, Bio sense). Access to the LV endocardium for the DLVI catheter (MyoStar™, Biosense) will be achieved using a retrograde transaortic approach via femoral artery (45). In each animal, 10 spatially discrete sites will be chosen for DLVI, which will be guided solely by the 3D $^{19}F/^{1}H$ MRI data. The LV tissue bordering the dense infarction region will be targeted with a mock-therapeutic, so as to test the spatial accuracy of the approach. At each injection site, 150 μl of a suspension of fluorescent-MPIO particles (Bangs Laboratories) will be delivered via the MyoStar catheter. These particles, sized 1-2 μm in diameter, are non-biodegradable. The linear distances between the injection sites and the apparent infarction border zone, as observed in the $^{19}F$ image, will be noted.

In Vivo MRI Post-DLVI—

On post-MI day 7, animals will be returned to the MR scanner to acquires spin-density-weighted $^{19}F$ and T2*-weighted $^{1}H$ images using similar methods as described above. The superparamagnetic MPIO deposition sites should be readily detectable as punctate sites of signal hypointensity in T2*-weighted images located in the infarction border zone. Animals will then be sacrificed and hearts removed en bloc and fixed. As before, using Amira software a volume-rendered, composite $^{19}F/^{1}H$ 3D image will be generated and saved as a DICOM file. These data will be analyzed by measuring the linear distances between the injection sites and the apparent infarction boundary zone, as seen by $^{19}F$.

MRI and Histology of Ex Vivo Hearts—

To further evaluate the DLVI accuracy, intact, fixed hearts will be imaged at very-high resolution using a 7 T instrument (Bruker). This scanner is equipped with a volume coil for uniform imaging, and the absence of cardiac motion will yield very high quality 3D images of the myocardium anatomy and inflammation distribution. $^{19}F/^{1}H$ MRI of the hearts will be performed using a RARE sequence to yield similar results as shown in FIGS. 3a and 3b. These image results will be placed into Amira software to generate volume-rendered $^{19}F/^{1}H$ 3D images as described above. These data will be analyzed quantitatively by measuring the linear distances between the injection sites and the apparent infarction boundary zone, as observed by $^{19}F$ MRI. Portions of the heart will then be paraffin-embedded, sectioned, and stained with H&E to visualize the inflammation boundary zones and putative injection sites; alternate slices will be used for fluorescence microscopy to visualize the fluorescent-MPIO particle deposits. These histology data will be used to confirm that the injection sites hit regions of pronounced inflammation. Distances between histologically-apparent border zone and fluorescence deposits will be measured.

The PFC enabled 3D $^{19}F$ image data will be used to reliably obtain precise coordinates for image-guided DLVI of test articles.

Example 9

DLVI Guided by PFC-Enhanced $^{19}F$ Images

Figure 5:
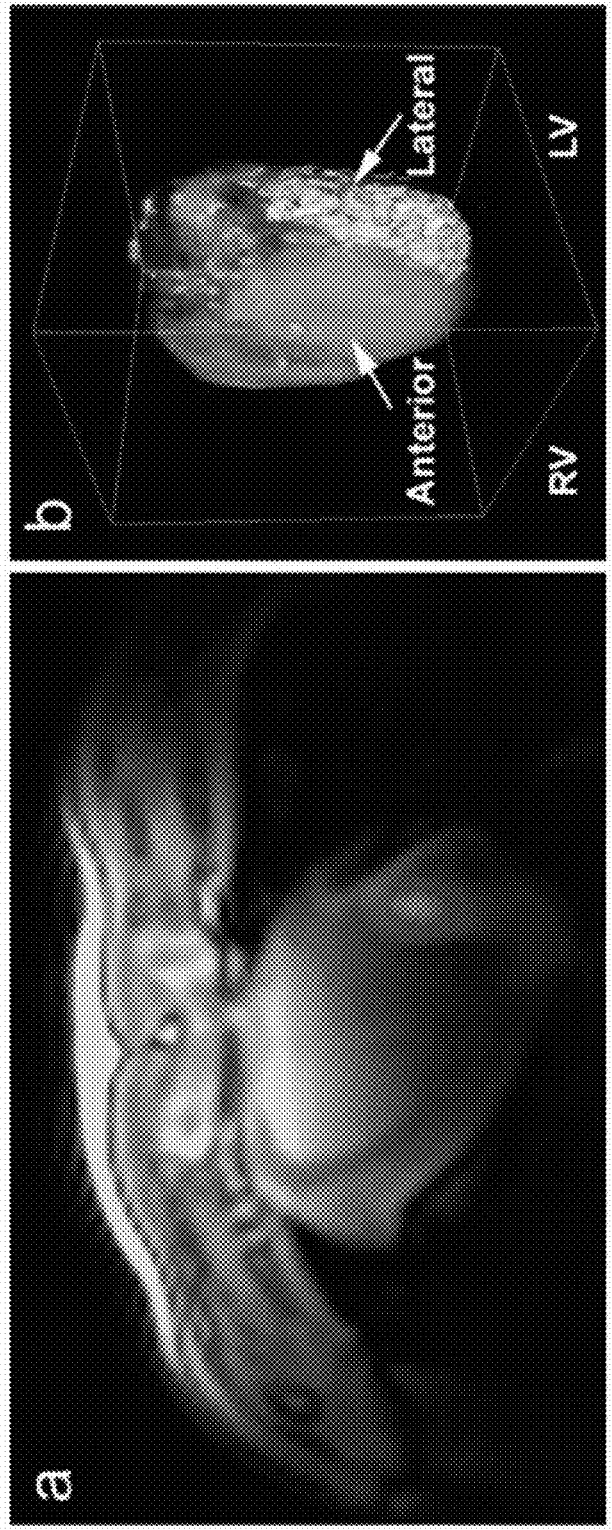
FIG. 5A-B shows results of a $^{19}$F MRI study, performed in a conventional clinical scanner, of inflammation in MI using PFC emulsion. (a) In an adult swine, the MI was induced by a transient catheterization of the left circumflex artery. Afterwards, PFC was infused intravenously. After 4 days, the swine was imaged using a Siemens 3 T clinical scanner with a 7 cm diameter $^{19}$F/$^1$H surface coil placed on the chest. Shown is a composite $^{19}$F/$^1$H scan. For $^{19}$F, the imaging time was 4 mins 16 per slice packet. The $^{19}$F image signal-to-noise ratio was ~18. ($^1$H FLASH imaging parameters were: TR/TE=164/1.2 ms, averages=1, slice thickness=4 mm, FOV=34×24.4 cm2, matrix size=256×184. $^{19}$F FLASH imaging parameters were TR/TE=500/6 ms, averages=16, slice thickness=4 mm, FOV=34×34 cm$^2$, matrix size=64×32). Panel (b) shows a rendering of a validating 3D MRI scan at 7 T (Bruker) of the same heart after being excised and fixed, where the $^{19}$F is in pseudo-color and the $^1$H is in grayscale.
Figure 8:
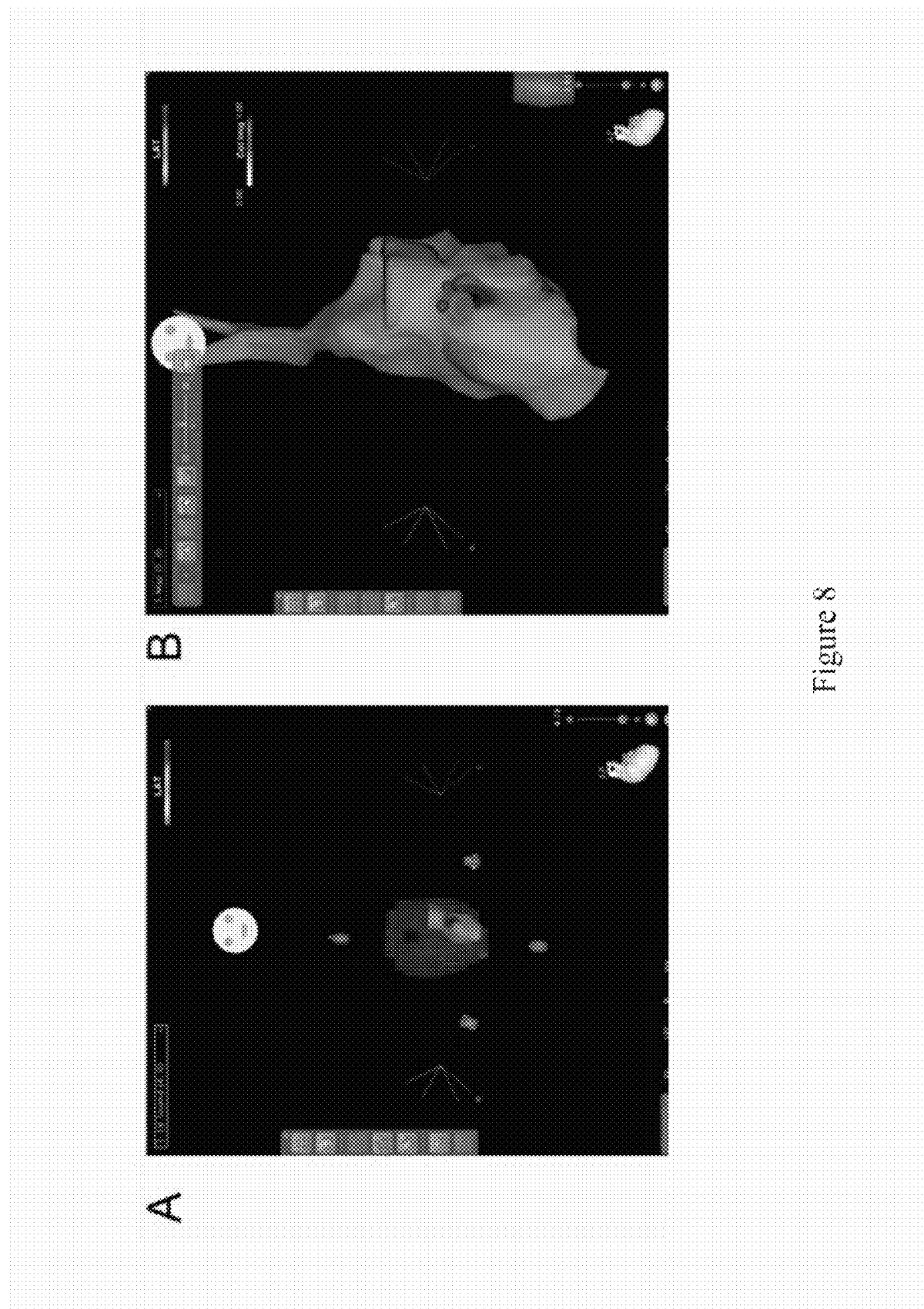
FIG. 8A-C show application of the clinical workflow as described FIG. 1 in the same porcine MI model of FIG. 5. (A) Using the 3D $^1$H MRI data set, the heart boundaries was segmented and rendered semi-transparent and pseudo-colored (brown), and the LV was also segmented and volume rendered (white). The $^{19}$F MRI data showing the 'hot-spots' of inflammation was superimposed onto the segmented $^1$H image of the LV and rendered in rainbow pseudo-color. The PFC cardiac image was spatially registered to the operative field using the thoracic fiducial markers (green ellipsoids) and commercial software (CartoMerge, Biosense). (B) shows the results of the catheter-based 3D Fast Anatomical Map (FAM) of the porcine LV overlaid onto the segmented MRI data of the LV (white translucent surface), and adequate registration of these two datasets was observed. The spatial location of the injection sites were recorded by the Biosense Webster system (small red spheres). (C) shows representative results of a 3D rendering (left panel) of the $^{19}$F (pseudo-color) and $^1$H data (grayscale) and 2D slices from this same dataset (right panels) showing the region of inflammation hot-spots (hot-iron, pseudo-color) acquired using $^{19}$F on an anatomical $^1$H background (grayscale). The arrows (right panel) show sites of needle wounding during injection of the mock-therapeutic in proximity to the inflammatory hot-spots.
Figure 8:
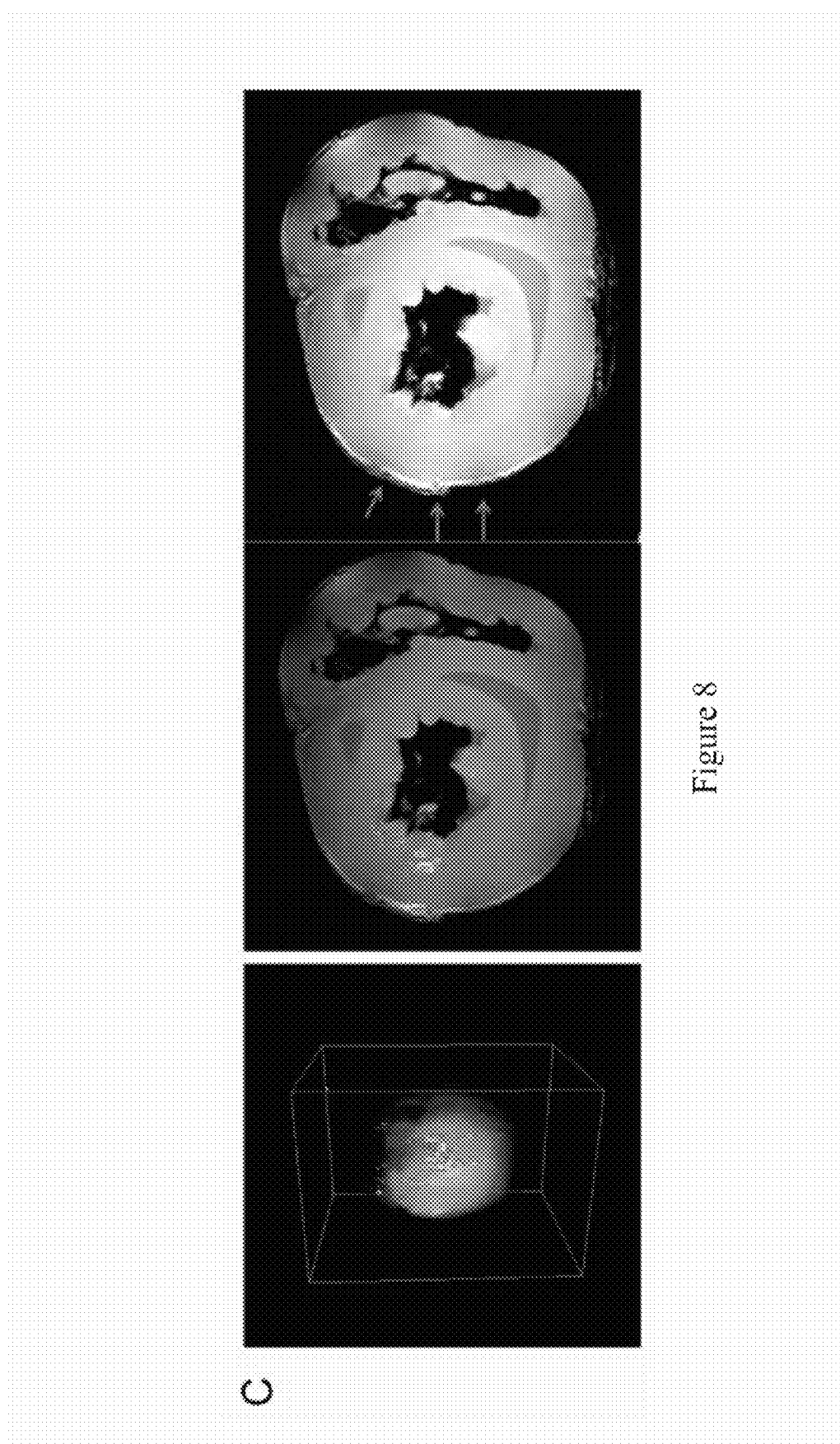

This experiment demonstrated DLVI guided by PFC-enhanced 19F images using the clinical workflow as described FIG. 1 in the same porcine MI model of FIG. 5. In this porcine MI model, the fluorocarbon emulsion was delivered intravenously immediately after infarct to in situ label inflammatory cells, predominately macrophages. On day 7 after infarct, $^{19}F$ and $^{1}H$ 3D MRI scans were acquired on the swine using a Siemens 3 T clinical scanner. Four fiducial markers (vitamin E capsules) were placed on the animal's torso in the image field of view prior to the scan. Additionally chest electrodes were placed on the animal to obtain an electrocardiogram signal during the scan to enable gated MRI data acquisitions in the same place in the cardiac cycle. Using the 3D $^{1}H$ MRI data set (FIG. 8A), the heart boundaries was segmented and rendered semi-transparent and pseudo-colored (brown), and the LV was also segmented and volume rendered (white). The $^{19}F$ MRI data showing the 'hot-spots' of inflammation was superimposed onto the segmented $^{1}H$ image of the LV and rendered in rainbow pseudo-color (FIG. 8A).

On post-MI day 14, the animal was brought to the clinical interventional cardiology suite. DLVI catheter navigation was assisted by a commercial magnetic tracking system (NOGA™, Biosense Webster, Diamond Bar, Calif.). The PFC cardiac image was spatially registered to the operative field using the thoracic fiducial markers (green ellipsoids) and commercial software (CartoMerge, Biosense). To validate the alignment of the MRI data in the interventional cardiac suite, the catheter-based 3D Fast Anatomical Map (FAM) feature in the Bio sense Webster system was used to create a surface rendering of the LV. FIG. 8B shows the results of the FAM of the porcine LV overlaid onto the segmented MRI data of the LV (white translucent surface), and adequate registration of these two datasets was observed. Access to the LV endocardium for the DLVI catheter (MyoStar™, Biosense) was achieved using a retrograde transaortic approach via femoral artery, and guided solely by the 3D $^{19}$F/$^{1}$H MRI data. The LV tissue bordering the infarction region was targeted with a mock-therapeutic (10 μl of a PBS), so as to test the spatial accuracy of the approach. At each injection site (N=5), the PBS was delivered via the MyoStar catheter. The spatial location of the injection sites were recorded by the Biosense Webster system (FIG. 8B, small red spheres).

To validate the results, the porcine was then sacrificed, the heart removed and fixed, and $^{19}$F/$^{1}$H images were acquired at high resolution using a 7T Bruker animal scanner. FIG. 8C shows representative results of a 3D rendering (left panel) of the $^{19}$F (pseudo-color) and $^{1}$H data (grayscale). Also shown in FIG. 8C (right panels), are 2D slices from this same dataset showing the region of inflammation hot-spots (hot-iron, pseudo-color) acquired using $^{19}$F on an anatomical $^{1}$H background (grayscale). The arrows (FIG. 8C, right panel) show sites of needle wounding during injection of the mock-therapeutic in proximity to the inflammatory hot-spots. The proximity of the sites of injection to the inflammatory hot-spots demonstrates the accuracy of the image-guided treatment.

Example 10

Image-Guided Biopsy of Liver Cancer

Subjects with liver cancer will receive a bolus of PFC emulsion which will enter into the reticuloendothelial system, including phagocytic cells of the liver and tumor associated macrophages. The 3D affected liver tissue pattern will be imaged using a clinical scanner and optimized MRI methods. V-Sense PFC emulsion (Celsense) will be used. In the healthy liver the MRI-apparent $^{19}$F distribution will be approximately uniform throughout the organ, but a lesioned liver will display visible regions of $^{19}$F heterogeneity and/or regions devoid of apparent $^{19}$F signal. The 3D affected tissue $^{19}$F pattern will be used as a map to select a cancerous tissue to biopsy. Biopsy navigation will be assisted by a commercial magnetic tracking system (NOGA™, Bio sense Webster, Diamond Bar, Calif.). The PFC liver image will be spatially registered to the operative field using the thoracic fiducial markers and commercial software (Biosense). The biopsy tissue will be analyzed histologically to confirm the accuracy of the biopsy.

This experiment demonstrates the accuracy of PFC image-guided biopsy.

Example 11

Image Guided Biopsy of Transplanted Kidney Undergoing Rejection

Subjects undergoing kidney transplant rejection will receive a bolus of PFC emulsion which will enter into the reticuloendothelial system, including phagocytic cells of the kidney and transplant associated macrophages. The 3D affected kidney tissue pattern will be imaged using a clinical scanner and optimized MRI methods. V-Sense PFC emulsion (Celsense) will be used. In a healthy kidney the MRI-apparent $^{19}$F distribution will be approximately uniform throughout the organ, but a kidney undergoing an inflammatory response will display visible regions of $^{19}$F heterogeneity and/or regions devoid of apparent $^{19}$F signal. The 3D affected tissue $^{19}$F pattern will be used as a map to select affected tissue to biopsy. Biopsy navigation will be assisted by a commercial magnetic tracking system (NOGA™, Biosense Webster, Diamond Bar, Calif.). The PFC kidney image will be spatially registered to the operative field using the thoracic fiducial markers and commercial software (Biosense). The biopsy tissue will be analyzed histologically to confirm the accuracy of the biopsy.

This experiment is expected to demonstrate the accuracy of PFC image-guided biopsy.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

1. Ahrens E T, Young W B, Xu H Y, Pusateri L K. Rapid quantification of inflammation in tissue samples using perfluorocarbon emulsion and fluorine-19 nuclear magnetic resonance. Biotechniques 2011; 50(4):229-234.
2. Hertlein T, Sturm V, Kircher S, Basse-Lusebrink T, Haddad D, Ohlsen K, Jakob P. Visualization of abscess formation in a murine thigh infection model of *staphylococcus aureus* by (19)F-Magnetic Resonance Imaging (MRI). PLoS ONE 2011; 6(3).
3. Hitchens T K, Ye Q, Eytan D F, Janjic J M, Ahrens E T, Ho C. (19)F MRI detection of acute allograft rejection with in vivo perfluorocarbon labeling of immune cells. Magn Reson Med 2011; 65(4):1145-1154.
4. Weise G, Basse-Luesebrink T C, Wessig C, Jakob P M, Stoll G. In vivo imaging of inflammation in the peripheral nervous system by (19)F MRI. Experimental Neurology 2011; 229(2):494-501.
5. Kampf T, Fischer A, Basse-Lusebrink T C, Ladewig G, Breuer F, Stoll G, Jakob P M, Bauer W R. Application of compressed sensing to in vivo 3D (19)F CSI. Journal of Magnetic Resonance 2010; 207(2):262-273.
6. Kadayakkara D, Ranganathan S, Young W B, Ahrens E T. Assaying macrophage activity in a murine model of inflammatory bowel disease using fluorine-19 MRI. Lab Invest. 2012; April; 92(4):636-45.
7. Mukherjee S, Gualandi C, Focarete M L, Ravichandran R, Venugopal J R, Raghunath M, Ramakrishna S. Elastomeric electro spun scaffolds of poly(1-lactide-co-trimethylene carbonate) for myocardial tissue engineering. Journal of Materials Science-Materials in Medicine 2011; 22(7):1689-1699.
8. Penn M S, Dong F, Klein S, Mayorga M E. Stem cells for myocardial regeneration. Clinical Pharmacology & Therapeutics 2011; 90(4):499-501.
9. Segers V F M, Lee R T. Biomaterials to enhance stem cell function in the heart. Circulation Research 2011; 109(8): 910-922.
10. Baumjohann D, Lutz M B. Non-invasive imaging of dendritic cell migration in vivo. Immunobiology 2006; 211(6-8):587-597.
11. Olasz E B, Lang L X, Seidel J, Green M V, Eckelman W C, Katz S I. Fluorine-18 labeled mouse bone marrow-derived dendritic cells can be detected in vivo by high resolution projection imaging. J Immunol Methods 2002; 260(1-2):137-148.

12. de Vries I J, Lesterhuis W J, Barentsz J O, Verdijk P, van Krieken J H, Boerman O C, Oyen W J, Bonenkamp J J, Boezeman J B, Adema G J, Bulte J W, Scheenen T W, Punt C J, Heerschap A, Figdor C G. Magnetic resonance tracking of dendritic cells in melanoma patients for monitoring of cellular therapy. Nat Biotechnol 2005; 23(11): 1407-1413.
13. Lautamaki R, Schuleri K H, Sasano T, Javadi M S, Youssef A, Merrill J, Nekolla S G, Abraham M R, Lardo A C, Bengel F M. Integration of infarct size, tissue perfusion, and metabolism by hybrid cardiac positron emission tomography/computed tomography evaluation in a porcine model of myocardial infarction. Circulation-Cardiovascular Imaging 2009; 2(4):299-305.
14. Godino C, Messa C, Gianolli L, Landoni C, Margonato A, Cera M, Stefano C, Cianflone D, Fazio F, Maseri A. Multifocal, Persistent cardiac uptake of 18-F-fluoro-deoxy-glucose detected by positron emission tomography in patients with acute myocardial infarction. Circulation Journal 2008; 72(11):1821-1828.
15. McAteer M A, Sibson N R, von zur Muhlen C, Schneider J E, Lowe A S, Warrick N, Channon K M, Anthony D C, Choudhury R P. In vivo magnetic resonance imaging of acute brain inflammation using microparticles of iron oxide. Nat Med 2007; 13(10):1253-1258.
16. Schmitz S A, Coupland S E, Gust R, Winterhalter S, Wagner S, Kresse M, Semmler W, Wolf K J. Superparamagnetic iron oxide-enhanced MRI of atherosclerotic plaques in Watanabe hereditable hyperlipidemic rabbits. Investigative Radiology 2000; 35(8):460-471.
17. Trivedi R A, Mallawarachi C, U-King-Im J M, Graves M J, Horsley J, Goddard M J, Brown A, Wang L Q, Kirkpatrick P J, Brown J, Gillard J H. Identifying inflamed carotid plaques using in vivo USPIO-enhanced MR imaging to label plaque macrophages. Arteriosclerosis Thrombosis and Vascular Biology 2006; 26(7):1601-1606.
18. Wu Y L, Ye Q, Foley L M, Hitchens T K, Sato K, Williams J B, Ho C. In situ labeling of immune cells with iron oxide particles: An approach to detect organ rejection by cellular MRI. Proc Natl Acad Sci USA 2006; 103(6): 1852-1857.
19. Yang Y D, Yang Y H, Yanasak N, Schumacher A, Hu T C C. Temporal and noninvasive monitoring of inflammatory-cell infiltration to myocardial infarction sites using micrometer-sized iron oxide particles. Magn Reson Med 2010; 63(1):33-40.
20. Chen W, Cormode D P, Fayad Z A, Mulder W J M. Nanoparticles as magnetic resonance imaging contrast agents for vascular and cardiac diseases. Wiley Interdisciplinary Reviews-Nanomedicine and Nanobiotechnology 2011; 3(2):146-161.
21. Liu W, Frank J A. Detection and quantification of magnetically labeled cells by cellular MRI. European Journal of Radiology 2009; 70(2):258-264.
22. Krafft M P. Fluorocarbons and fluorinated amphiphiles in drug delivery and biomedical research. Adv Drug Deliv Rev 2001; 47(2-3):209-228. Helfer B M, Nelson A D, Janjic J M, Ahrens E T, Gil R R, Kalinski P, de Vries J, Mailliard R B. Using a $^{19}F$ MRI tracer agent for in vivo tracking of human dendritic cell vaccines. Proceedings of the International Society for Magn Reson Med, Seventeenth Scientific Meeting 2009; abstract #522.
23. Helfer B M, Balducci A, Nelson A D, Janjic J M, Gil R R, Kalinski P, De Vries I J M, Ahrens E T, Mailliard R B. Functional assessment of human dendritic cells labeled for in vivo F-19 magnetic resonance imaging cell tracking. Cytotherapy 2010; 12(2):238-250.
24. Ahrens E T, Flores R, Xu H Y, Morel P A. In vivo imaging platform for tracking immunotherapeutic cells. Nature Biotechnology 2005; 23(8):983-987.
25. Srinivas M, Morel P A, Ernst L A, Laidlaw D H, Ahrens E T. Fluorine-19 MRI for visualization and quantification of cell migration in a diabetes model. Magn Reson Med 2007; 58:725-734.
26. Kadayakkara D K, Beatty P L, Turner M S, Janjic J M, Ahrens E T, Finn O J. Inflammation driven by overexpression of the hypoglycosylated abnormal mucin 1 (MUC1) links inflammatory bowel disease and pancreatitis. Pancreas 2010; 39(4):510-515.
27. Janjic J M, Srinivas M, Kadayakkara D K K, Ahrens E T. Self-delivering nanoemulsions for dual fluorine-19 MRI and fluorescence detection. Journal of the American Chemical Society 2008; 130(9):2832-2841.
28. Ruiz-Cabello J, Walczak P, Kedziorek D A, Chacko V P, Schmieder AH, Wickline S A, Lanza G M, Bulte J W. In vivo "hot spot" MR imaging of neural stem cells using fluorinated nanoparticles. Magn Reson Med 2008; 60(6): 1506-1511.
29. Partlow K C, Chen J, Brant J A, Neubauer A M, Meyerrose T E, Creer M H, Nolta J A, Caruthers S D, Lanza G M, Wickline S A. $^{19}F$ magnetic resonance imaging for stem/progenitor cell tracking with multiple unique perfluorocarbon nanobeacons. FASEB J 2007; 21(8):1647-1654.
30. Kim Y C, Narayanan S S, Nayak K S. Accelerated three-dimensional upper airway MRI using compressed sensing. Magn Reson Med 2009; 61(6):1434-1440.
31. Liang D, Liu B, Wang J J, Ying L. Accelerating SENSE using compressed sensing. Magn Reson Med 2009; 62(6): 1574-1584.
32. Schirra C O, Weiss S, Krueger S, Pedersen S F, Razavi R, Schaeffter T, Kozerke S. Toward true 3D visualization of active catheters using compressed sensing. Magn Reson Med 2009; 62(2):341-347.
33. Ajraoui S, Lee K J, Deppe M H, Parnell S R, Parra-Robles J, Wild J M. Compressed sensing in hyperpolarized He-3 lung MRI. Magn Reson Med 2010; 63(4):1059-1069.
34. Kampf T, Fischer A, Basse-Lusebrink T C, Ladewig G, Breuer F, Stoll G, Jakob P M, Bauer W R. Application of compressed sensing to in vivo 3D F-19 CSI. Journal of Magnetic Resonance 2010; 207(2):262-273.
35. Yerly J, Lauzon M L, Chen H S, Frayne R. A simulation-based analysis of the potential of compressed sensing for accelerating passive MR catheter visualization in endovascular therapy. Magn Reson Med 2010; 63(2):473-483.
36. Lustig M, Donoho D, Pauly J M. Sparse MRI: The application of compressed sensing for rapid MR imaging. Magn Reson Med 2007; 58(6):1182-1195.
37. http://www.fda.gov/downloads/Drugs/GuidanceComplianceRegulatoryInformation/Guidances/ucm071600.pdf
38. Patten R D, Aronovitz M J, Deras-Mejia L, Pandian N G, Hanak G G, Smith J J, Mendelsohn M E, Konstam M A. Ventricular remodeling in a mouse model of myocardial infarction. American Journal of Physiology-Heart and Circulatory Physiology 1998; 274(5):H1812-H1820.
39. Schwartzman D, Chang I, Michele J J, Mirotznik M S, Foster K R. Electrical impedance properties of normal and chronically infarcted left ventricular myocardium. Journal of Interventional Cardiac Electrophysiology 1999; 3(3):213-224.
40. Boada F E, Shen G X, Chang S Y, Thulborn K R. Spectrally weighted twisted projection imaging: Reducing T-2 signal attenuation effects in fast three-dimensional sodium imaging. Magn Reson Med 1997; 38(6):1022-1028.
41. Schwartzman D, Kuck K H. Anatomy-guided linear atrial lesions for radiofrequency catheter ablation of atrial fibrillation. Pace-Pacing and Clinical Electrophysiology 1998; 21(10):1959-1978.
42. Zhong H, Lacomis J M, Schwartzman D. On the accuracy of CartoMerge for guiding posterior left atrial ablation in man. Heart Rhythm 2007; 4(5):595-602.
43. Zhong H, Schwartzman D. An improved algorithm for intraoperative registration of computed tomographic left atrial images. Europace 2011; 13(3):383-388.
44. Kastrup J, Jorgensen E, Ruck A, Tagil K, Glogar D, Ruzyllo W, Botker H E, Dudek D, Drvota V, Hesse B, Thuesen L, Blomberg P, Gyongyosi M, Sylven C, Euroinject One G. Direct intramyocardial plasmid vascular endothelial growth factor-A(165)-gene therapy in patients with stable severe angina pectoris—A randomized double-blind placebo-controlled study: The Euroinject One trial. Journal of the American College of Cardiology 2005; 45(7):982-988.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

What is claimed is:

1. A method for image-guided treatment of a subject with a condition associated with an inflammatory response in an internal organ comprising:
   a) administering a $^{19}$F MRI fluorocarbon imaging reagent to said subject to label inflammatory cells,
   b) performing $^{19}$F MRI of the subject to detect labeled inflammatory cells,
   c) identifying, for the internal organ, boundaries between healthy and affected tissue in the subject using the $^{19}$F MRI data from step (b), and
   d) administering a medicament to the internal organ based on data obtained in step (c) to treat the condition.

2. The method of claim 1, wherein step (b) comprises performing $^{19}$F MRI in a region of interest of the subject.

3. The method of claim 1, wherein said performing $^{19}$F MRI step is achieved by a sparse scanning of k-space.

4. The method of claim 1, wherein step (b) further comprises performing $^{1}$H MRI and step (c) further comprises using the $^{1}$H MRI data from step (b).

5. The method of claim 1, wherein step (d) uses the data from step (c) as a 3D pattern of inflammation for guiding delivery of the medicament.

6. The method of claim 1, wherein step (d) comprises administering the medicament at one or more boundaries between healthy and affected tissue.

7. The method of claim 1, wherein the internal organ is selected from the group consisting of heart, kidney, bladder, liver, pancreas, intestine, appendix, esophagus, stomach, rectum, gall bladder, prostate, uterus, ovary, lung, brain, spinal cord, or spleen.

8. The method of claim 7, wherein the internal organ is the heart.

9. The method of claim 8, wherein the condition is cardiac arrest or myocardial infarction.

10. The method of claim 9, wherein $^{19}$F MRI is performed within one to seven days of the myocardial infarction.

11. The method of claim 8, wherein the medicament is administered by direct left ventricle injection (DLVI).

12. The method of claim 1, wherein the medicament is selected from a small molecule, protein, nucleic acid, or a cellular therapeutic.

13. The method of claim 12, wherein the cellular therapeutic comprises stem cells.

14. The method of claim 1, wherein the medicament is administered endoscopically or by a catheter.

15. The method of claim 1, wherein the fluorocarbon imaging reagent comprises a perfluoropolyether.

16. The method of claim 15, wherein the fluorocarbon imaging reagent comprises a perfluoroctylbromide.

17. The method of claim 1, wherein the fluorocarbon imaging reagent is conjugated to an inflammatory cell targeting moiety.

18. The method of claim 1, wherein the fluorocarbon imaging reagent is formulated as an emulsion.

19. The method of claim 18, wherein the emulsion comprises particles having a mean diameter of between 30 and 500 nm.

20. The method of claim 1, wherein the fluorocarbon comprises a perfluorinated polyether having an average formula:

$$XO(Y-O)_nZ$$

wherein Y is selected from the group consisting of:

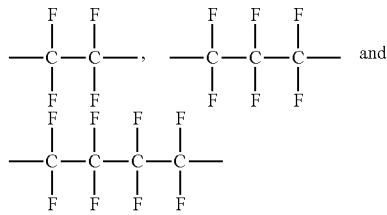

wherein n is an integer from 8 to 20; wherein X and Z are the same and are selected from the group consisting of perfluoroalkyls, perfluoroethers, fluoroalkyls terminated with fluoroacyl, carboxyl, amide or ester, methylols, acid chlorides, amides, amidines, acrylates and esters.

21. The method of claim 1, wherein the fluorocarbon imaging reagent further comprises a detection moiety is selected from the group consisting of: a fluorescent detection moiety and a PET detection moiety.

22. A method for image-guided treatment of a subject with a condition associated with an inflammatory response in an internal organ comprising:
   a) providing $^{19}$F MRI data identifying boundaries between healthy and affected tissue of the internal organ of the subject, which subject was previously administered a $^{19}$F MRI fluorocarbon imaging reagent to label inflammatory cells, and
   b) administering a medicament to the internal organ based on data obtained in step (a) to treat the condition.

23. The method of claim 22, wherein step (b) comprises administering the medicament at one or more boundaries between healthy and affected tissue.

24. The method of claim 22, wherein the internal organ is selected from the group consisting of heart, kidney, bladder, liver, pancreas, intestine, appendix, esophagus, stomach, rectum, gall bladder, prostate, uterus, ovary, lung, brain, spinal cord, or spleen.

25. The method of claim 24, wherein the internal organ is the heart.

26. The method of claim 25, wherein the condition is cardiac arrest or myocardial infarction.

27. The method of claim 25, wherein the medicament is administered by direct left ventricle injection (DLVI).

28. The method of claim 22, wherein the medicament is selected from a small molecule, protein, nucleic acid, or a cellular therapeutic.

29. The method of claim 28, wherein the medicament comprises stem cells.

30. The method of claim 22, wherein the medicament is administered endoscopically or by a catheter.

31. A method for image-guided diagnosis of a subject with a condition associated with an inflammatory response in an internal organ comprising:
   a) administering a $^{19}$F MRI fluorocarbon imaging reagent to said subject to label inflammatory cells,
   b) performing $^{19}$F MRI of the subject to detect labeled inflammatory cells,
   c) identifying, for the internal organ, boundaries between healthy and affected tissue in the subject using the $^{19}$F MRI data from step (b), and
   d) performing a diagnostic procedure on the internal organ based on data obtained in step (c).

32. The method of claim 31, wherein the internal organ is selected from the group consisting of heart, kidney, bladder, liver, pancreas, intestine, appendix, esophagus, stomach, rectum, gall bladder, prostate, uterus, ovary, lung, brain, spinal cord, or spleen.

33. The method of claim 32, wherein the internal organ is the heart.

34. The method of claim 33, wherein the condition is cardiac arrest, myocardial infarction, or cancer.

35. The method of claim 31, wherein the internal organ is a transplanted organ.

36. The method of claim 31, wherein the diagnostic procedure is a biopsy.

* * * * *